US008173598B2

(12) United States Patent
Sroussi

(10) Patent No.: US 8,173,598 B2
(45) Date of Patent: May 8, 2012

(54) MYELOID PROTEIN ACTIVATION OF ANTI-INFLAMMATORY AND ANTI-HYPOXIC PATHWAY

(75) Inventor: Herve Y. Sroussi, Glencoe, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/095,622

(22) Filed: Apr. 27, 2011

(65) Prior Publication Data

US 2011/0201542 A1 Aug. 18, 2011

Related U.S. Application Data

(63) Continuation of application No. 12/551,225, filed on Aug. 31, 2009, now abandoned.

(60) Provisional application No. 61/155,208, filed on Feb. 25, 2009, provisional application No. 61/147,599, filed on Jan. 27, 2009, provisional application No. 61/138,270, filed on Dec. 17, 2008, provisional application No. 61/093,100, filed on Aug. 29, 2008.

(51) Int. Cl.
*A61K 38/00* (2006.01)

(52) U.S. Cl. .................................................. 514/15.1
(58) Field of Classification Search ..................... 514/12
See application file for complete search history.

(56) References Cited

U.S. PATENT DOCUMENTS

| | | | |
|---|---|---|---|
| 5,731,166 | A | 3/1998 | Geczy et al. |
| 5,776,348 | A | 7/1998 | Selengut et al. |
| 6,620,790 | B2 | 9/2003 | Siegenthaler |
| 7,081,345 | B1 | 7/2006 | Roecklin et al. |
| 2006/0281674 | A1 | 12/2006 | Tessier et al. |
| 2007/0123455 | A1 | 5/2007 | Palefsky et al. |

OTHER PUBLICATIONS

Brun et al., APMIS, 103, 233-240, 1995.*
Prosecution history for parent U.S. Appl. No. 12/551,225, filed Aug. 31, 2009 (downloaded Apr. 25, 2011), last document dated Mar. 4, 2011, 81 pp.
Aguiar-Passeti et al. (1997) "Epithelioid Cells from Foreign-Body Granuloma Selectively Express the Calcium-Binding Protein MRP-14, A Novel Down-Regulatory Molecule of Macrophage Activation," *J. Leuk. Biol.* 62:852-858.
Asfaha et al. (2007) "Protease-Activated Receptor-4: A Novel Mechanism of Inflammatory Pain Modulation," *Br. J. Pharmacol.* 150:176-185; published online Dec. 18, 2006.
Broussas et al. (2002) "Adenosine Inhibits Tissue Factor Expression by LPS-Stimulated Human Monocytes: Involvement of the A3 Adenosine Receptor," *Thromb. Haemost.* 88:123-130.
Brun et al. (1992) "Calprotectin in Patients with Rheumatoid Arthritis: Relation to Clinical and Laboratory Variables of Disease Activity," *J. Rheumatol.* 19:859-862.
Cave et al. (2006) "NADPH Oxidases in Cardiovascular Health and Disease," *Antioxid Redox Signal* 8:691-728.

Chen et al. (2006) "ATP Release Guides Neutrophil Chemotaxis via P2Y2 and A3 Receptors," *Science* 314:1792-1795.
Chen et al. (2006) "Activation of Adenosine A3 Receptors Reduces Ischemic Brain Injury in Rodents," *J. Neurosci. Res.* 84:1848-1855.
Ciapetti et al. (1998) "Fluorescent Microplate Assay for Respiratory Burst of PMNs Challenged in Vitro with Orthopedic Metals," *J. Biomed. Mater. Res.* 41:455-460.
Cornish et al. (1996) "S100 Protein CP-10 Stimulates Myeloid Cell Chemotaxis without Activation," *J. Cell. Physiol.* 166:427-437.
Covic et al. (2002) "Pepducin-Based Intervention of Thrombin-Receptor Signaling and Systemic Platelet Activation," *Nat. Med.* 8:1161-1165.
Cumashi et al. (2001) "Neutrophil Proteases can Inactivate Human PAR3 and Abolish the Co-Receptor Function of PAR3 on Murine Platelets," *Thromb. Haemost.* 85:533-538.
Dale et al. (2006) "The C-Terminus of Murine S100A9 Protein Inhibits Hyperalgesia Induced by the Agonist Peptide of Protease-Activated Receptor 2 (PAR2)," *Br. J. Pharmacol.* 149:374-384.
Daley et al. (2005) "Modulation of Macrophage Phenotype by Soluble Product(s) Released from Neutrophils," *J. Immunol.* 174:2265-2272.
Decoursey et al. (2005) "Regulation and Termination of NADPH Oxidase Activity," *Cell. Mol. Life Sci.* 62:2173-2193.
Dovi et al. (2003) "Accelerated Wound Closure in Neutrophil-Depleted Mice," *J. Leukoc. Biol.* 73:448-455.
Dunlop et al. (1991) "Calprotectin in Cerebrospinal Fluid of the HIV Infected: A Diagnostic Marker of Opportunistic Central Nervous System Infection," *Scand. J. Infect. Dis.* 23(6):687-689.
Eckert et al. (1995) "The Surgical Implications of Chronic Granulomatous Disease," *Am. J. Surg.* 169:320-323.
Edgeworth et al. (1991) "Identification of p8, 14 as a Highly Abundant Heterodimeric Calcium Binding Protein Complex of Myeloid Cells," *J. Biol. Chem.* 266:7706-7713.
Farhadi et al. (2002) "Modulatory Effects of Plasma and Colonic Milieu of Patients with Ulcerative Colitis on Neutriphil Reactive Oxygen Species Production in Presence of a Novel Antioxidant, Rebamipide," *Dig. Dis. Sci.* 47:1342-1348.
Fessatou et al. (2005) "Severe Anemia and Neutropenia Associated with Hyperzincemia and Hypercalprotectinemia," *J. Pediatr. Hematol. Oncol.* 27:477-480.
Gabrielsen et al. (Aug. 1986) "Epidermal and Dermal Distribution of a Myelomonocytic Antigen (L1) Shared by Epithelial Cells in Various Inflammatory Skin Diseases," *J. Am. Acad. Dermatol.* 15(2):173-179.
Gajendrareddy et al. (Web Release Nov. 21, 2004) "Hyperbaric Oxygen Therapy Ameliorates Stress-Impaired Dermal Wound Healing," *Brain Behav. Immun.* 19:217-222.

(Continued)

*Primary Examiner* — Maryam Monshipouri
(74) *Attorney, Agent, or Firm* — Greenlee Sullivan P.C.

(57) ABSTRACT

Provided are methods to enhance healing of wounds and tissue, especially during or pursuant to psychological and/or physical stress and to protect tissue from deleterious effects associated with oxidative, psychological and/or physical stress, including but not limited to extreme exertion, ischemia, infarct, and damage associated with reperfusion of ischemic or transplanted tissues.

15 Claims, 12 Drawing Sheets

OTHER PUBLICATIONS

Glaser et al. (1999) "Stress-Related Changes in Proinflammatory Cytokine Production in Wounds," *Arch. Gen Psychiatry* 56:450-456.

Godbout et al. (2006) "Stress-Induced Immune Dysregulation: Implications for Wound Healing, Infectious Disease and Cancer," *J. Neuroimmune Pharmacol.* 1:421-427.

Golden et al. (1996) "Calprotectin as a Marker of Inflammation in Cystic Fibrosis," *Arch. Dis. Child* 74:136-139.

Gordillo et al. (2003) "Revisiting the Essential Role of Oxygen in Wound Healing," *Am. J. Surg.* 186:259-263.

Guerreiro et al. (2005) "Spontaneous Neutrophil Activation in HTL-1 Infected Patients," *Braz. J. Infect. Dis.* 9:510-514.

Halle et al. (1997) "Enhancing Adenosine A1 Receptor Binding Reduces Hypoxic-Ischemic Brain Injury in Newborn Rates," *Brain Res.* 759:309-312.

Harrison et al. (Mar. 26, 1999) "Oxidation Regulates the Inflammatory Properties of the Murine S100 Protein S100A8," *J. Biol. Chem.* 274(13):8561-8569.

Houle et al. (2005) "Neutrophils and the Kallikrein-Kinin System in Proteinase-Activated Receptor 4-Mediated Inflammation on Rodents," *Br. J. Pharmacol.* 146:670-678.

Hoxie et al. (Jun. 25, 1993) "Internalization and Recycling of Activated Thrombin Receptors," *J. Biol. Chem.* 268(18):13756-13763.

Hsieh et al. (1994) "Decreased Spontaneous and Lipopolysaccharide Stimulated Production of Interleukin 8 by Polymorphonuclear Neutrophils of Patients with Active Systemic Lupus Erythematosus," *Clin. Exp. Rheumatol.* 12:627-633.

Jinquan et al. (1996) "Psoriasin: A Novel Chemotactic Protein," *J. Invest. Dermatol.* 107:5-10.

Jung et al. (2008) "Combined Use of Myeloid-Related Protein 8/14 and Procalcitonin as Diagnostic Markers for Acute Allograft Rejection in Kidney Transplantation Recipients," *Transpl. Immunol.* 18:338-343; available online Oct. 29, 2007.

Kahn et al. (1999) "Protease-Activated Receptors 1 and 4 Mediate Activation of Human Platelets by Thrombin," *J. Clin. Invest.* 103:879-887.

Kannan, S. (2002) "Role of Protease-Activated Receptors in Neutrophil Degranulation," *Med. Hypotheses* 59(3):266-267.

Kerkhoff et al. (Dec. 10, 1998) "Novel Insights into Structure and Function of MRP8 (S100A8) and MRP14 (S100A9)," *Biochim. Biophys. Acta Mol. Cell. Res.* 1448(2):200-211.

Kiecolt-Glaser et al. (Nov. 4, 1995) "Slowing of Wound Healing by Psychological Stress," *Lancet* 346:1194-1196.

Kilpatrick et al. (Apr. 1, 1991) "Inhibition of Human Neutrophil Superoxide Generation by Alpha 1-Antichymotrypsin," *J. Immunol.* 146:2388-2393.

Klempt et al. (1997) "The Heterodimer of the $Ca^{2+}$-Binding Proteins MRP8 and MRP14 Binds Arachidonic Acid," *FEBS Lett.* 408:81-84.

Koethe et al. (2000) "Neutrophil Priming by Cigarette Smoke Condensate and a Tobacco Anti-Idiotypic Antibody," *Am. J. Pathol.* 157:1735-1743.

Komada et al. (Mar. 27, 1996) "Novel Specific Chemotactic Receptor for S100L Protein on Guinea Pig Eosinophils," *Biochem. Biophys. Res. Commun.* 220(3):871-874.

Lebel et al. (1992) "Evaluation of the Probe 2',7'-Dichlorofluorescin as an Indicator of Reactive Oxygen Species Formation and Oxidative Stress," *Chem. Res. Toxicol.* 5:227-231.

Leger et al. (2006) "Blocking the Protease-Activated Receptor 1-4 Heterodimer in Platelet-Mediated Thrombosis," *Circulation* 113:1244-1254.

Levy et al. (2006) "The Adenosine System Selectively Inhibits TLR-Mediated TNF-Alpha Production in the Human Newborn," *J. Immunol.* 177:1956-1966.

Lügering et al. (1995) "Immunohistochemical Distribution and Serum Levels of the $Ca^{2+}$-Binding Proteins MRP8, MRP14 and their Heterodimeric Form MRP8/14 in Crohn's Disease," *Digestion* 56(5):406-414.

Lügering et al. (1995) "Serum 27E10 antigen: a new potential marker for staging HIV disease" *Clin. Exp. Immunol.* 101:249-253.

Marionnet et al. (2003) "Modulation of Gene Expression Induced in Human Epidermis by Environmental Stress In Vivo," *J. Invest. Dermatol.* 121:1447-1458.

Marucha et al. (1998) "Mucosal Wound Healing is Impaired by Examination Stress," *Psychosom. Med.* 60:362-365.

Mercado et al. (2002) "Restraint Stress Alters the Expression of Interleukin-1 and Keratinocyte Growth Factor at the Wound Site: An In Situ Hybridization Study," *Neuroimmunol.* 129:74-83.

Mohanty et al. (1997) "A Highly Sensitive Fluorescent Micro-Assay of $H_2O_2$ Release from Activated Human Leukocytes Using a Dihydroxyphenoxazine Derivative," *J. Immunol. Methods* 202:133-141.

Muller et al. (1994) "Elevated Serum Calprotectin Levels in HIV-Infected Patients: The Calprotectin Response During ZDV Treatment is Associated with Clinical Events," *J. Acquir. Immune. Defic. Syndr.* 7:931-939.

Nagpal et al. (Dec. 1996) "Negative Regulation of Two Hyperproliferative Keratinocyte Differentiation Markers by a Retinoic Acid Receptor-Specific Retinoid: Insight into the Mechanism of Retinoid Action in Psoriasis," *Cell. Growth Differ.* 7:1783-1791.

Nakamura et al. (2000) "The Association of Calprotectin Level in Gingival Crevicular Fluid with Gingival Index and the Activities of Collagenase and Aspartate Aminotransferase in Adult Periodontitis Patients," *J. Periodontol.* 71:361-367.

Ossovskaya et al. (2004) "Protease-Activated Receptors: Contribution to Physiology and Disease," *Physiol. Rev.* 84:579-621.

Padgett et al. (1998) Restraint Stress Slows Cutaneous Wound Healing in Mice, *Brain Behav. Immun.* 12:64-73.

Passey et al. (Oct. 1999) "S100A8: Emerging Functions and Regulation," *J. Leukoc Biol.* 66:549-556.

Pham, C.T. (2006) "Neutrophil Serine Proteases: Specific Regulators of Inflammation," *Nat. Rev. Immunol.* 6:541-550.

Pham, C.T. (2008) "Neutrophil Serine Proteases Fine-Tune the Inflammatory Response," *Int. J. Biochem. Cell Biol.* 40:1317-1333.

Rallabhandi et al. (Sep. 5, 2008) "Analysis of Proteinase-Activated Receptor 2 and TLR Signal Transduction: A Novel Paradigm for Receptor Cooperativity," *J. Biol. Chem.* 283:24314-24325 (published online Jul. 11, 2008).

Rammes et al. (Apr. 4, 1997) "Myeloid-Related Protein (MRP) 8 and MRP14, Calcium-Binding Proteins of the S100 Family, are Secreted by Activated Monocytes via a Novel, Tubulin-Dependent Pathway," *J. Biol. Chem.* 272(14):9496-9502.

Reece et al. (2006) "Comparison of Systemic and Retrograde Delivery of Adenosine A2A Agonist for Attenuation of Spinal Cord Injury After Thoracic Aortic Cross-Clamping," *Ann. Thorac. Surg.* 81:902-909.

Reeves et al. (2002) "Killing Activity of Neutrophils is Mediated Through Activation of Proteases by K+ Flux," *Nature* 416:291-297.

Rojas et al. (2002) "Stress-Induced Susceptibility to Bacterial Infection During Cutaneous Wound Healing," *Brain Behav. Immun.* 16:74-84.

Roth et al. (2003) "Chemotactic Activity of S100A8 and S100A9," *J. Immunol.* 171:5651.

Ryckman et al. (2003) "Proinflammatory Activities of S100: Proteins S100A8, S100A9, and S100A8/A9 Induce Neutrophil Chemotaxis and Adhesion," *J. Immunol.* 170:3233-3242.

Ryckman et al. (2004) "Monosodium Urate Monohydrate Crystals Induce the Release of the Proinflammatory Protein S100A8/A9 from Neutrophils," *J. Leukoc. Biol.* 76:433-440.

Saito et al. (2002) "Hyperzincemia with Systemic Inflammation: A Heritable Disorder of Calprotectin Metabolism with Rheumatic Manifestations," *J. Pediatr.* 140:267-269.

Sambrano et al. (2000) "Cathepsin G Activates Protease-Activated Receptor-4 in Human Platelets," *J. Biol. Chem.* 275:6819-6823.

Sampson et al. (2002) "Hyperzincaemia and Hypercalprotectinaemia: A New Disorder of Zinc Metabolism," *Lancet* 360:1742-1745.

Savill et al. (1989) "Macrophage Phagocytosis of Aging Neutrophils in Inflammation. Programmed Cell Death in the Neutrophil Leads to its Recognition by Macrophages," *J. Clin. Invest.* 83:865-875.

Slofstra et al. (2007) "Protease-Activated Receptor-4 Inhibition Protects from Multiorgan Failure in Murine Model of Systemic Inflammation," *Blood* 110:3176-3182 (Prepublished online Jul. 19, 2007).

Sroussi et al. (Mar. 2007) "Oxidation of Methionine 63 and 83 Regulates the Effect of S100A9 on the Migration of Neutrophils in Vitro," *J. Leukoc. Biol.* 81:818-824.

Sroussi et al. (2006) "S100A8 Triggers Oxidation-Sensitive Repulsion of Neutrophils," *J. Dent. Res.* 85:829-833.

Sroussi et al. (Apr. 2010) "S100A8 and S100A9 Inhibit Neutrophil Oxidative Metabolism in Vitro: Involvement of Adenosine Metabolites," *Free Radic. Res.* 44(4):389-396 (Prepublished online Feb. 12, 2010).

Sroussi et al. (Aug. 2009) "Ala42S100A8 Ameliorates Psychological-Stress Impaired Cutaneous Wound Healing," *Brain Behav. Immun.* 23(6):755-759 (Prepublished online Mar. 29, 2009).

Sroussi et al. (Jan. 2009) "Substitution of Methionine 63 or 83 in S100A9 and Cysteine 42 in S100A8 Abrogate the Antifungal Activities of S100A8/A9 Potential Role for Oxidative Regulation," *FEMS Immunol. Med. Microbiol.* 55(1):55-61 (Prepublished online Dec. 12, 2008).

Strande et al. (Mar. 2008) "Inhibiting Protease-Activated Receptor 4 Limits Myocardial Ischemia/Reperfusion Injury in Rat Hearts by Unmasking Adenosine Signaling," *J. Pharmacol. Exp. Ther.* 324:1045-1054 (Prepublished online Nov. 19, 2007).

Sun et al. (Jan. 2008) "Adenosine A2A Receptor Agonists Inhibit Lipopolysaccharide-Induced Production of Tumor Necrosis Factor-Alpha by Equine Monocytes," *Vet. Immunol. Immunopathol.* 121:91-100 (Prepublished online Aug. 25, 2007).

Sweet et al. (2001) "Salivary Calprotectin Levels Are Raised in Patients with Oral Candidiasis of Sjogren's Syndrome but Decreased by HIV Infection," *Oral Microbiol Immunol.* 16:119-123.

Tan et al. (2000) "Superoxide Produced by Activated Neutrophils Efficiently Reduces the Tetrazolium Salt, WST-1 to Produce a Soluble Formazan: A Simple Colorimetric Assay for Measuring Respiratory Burst Activation and for Screening Anti-Inflammatory Agents," *J. Immunol. Methods* 238:59-68.

Thomas et al. (1995) "Cutaneous Wound Healing: A Current Perspective," *J. Oral Maxillofac. Surg.* 53:442-447.

Thorey et al. (2001) "The $Ca^{2+}$-binding Proteins S100A8 and S100A9 Are Encoded by Novel Injury-Regulated Genes," The Journal of Biological Chemistry 276(38):35818-35825.

Tibble et al. (2001) "Fecal Calprotectin as an Index of Intestinal Inflammation," *Drugs Today* 37:85-96.

Tugizov et al. (2005) "Inhibition of Human Papillomavirus Type 16 E7 Phosphorylation by the S100 MRP-8/14 Protein Complex," *J. Virol.* 79:1099-1112.

Van Der Hoeven et al. (Sep. 2008) "Activation of the A(3) Adenosine Receptor Suppresses Superoxide Production and Chemotaxis of Mouse Bone Marrow Neutrophils," *Mol. Pharmacol.* 74:685-696 (Prepublished online Jun. 26, 2008).

Vogl et al. (Sep. 2007) "Mrp8 and Mrp14 are Endogenous Activators of Toll-Like Receptor 4, Promoting Lethal, Endotoxin-Induced Shock," *Nat. Med.* 13:1042-1049 (Prepublished online Sep. 2, 2007).

Wilkinson et al. (1988) "Expression Pattern of Two Related Cystic Fibrosis-Associated Calcium-Binding Proteins in Normal and Abnormal Tissues," *J. Cell. Sci.* 91:221-230.

Yui et al. (2003) "Calprotectin (S100A8/S100A9), an Inflammatory Protein Complex from Neutrophils with a Broad Apoptosis-Inducing Activity," *Biol. Pharm. Bull.* 26:753-760.

Zahler et al. (1997) "The Function of Neutrophils Isolated by a Magnetic Antibody Cell Separation Technique is Not Altered in Comparison to a Density Gradient Centrifugation Method," *J. Immunol. Methods* 200:173-179.

Zarbock et al. (Mar. 2007) "Platelet-Neutrophil-Interactions: Linking Hemostasis and Inflammation," *Blood Rev.* 21:99-111 (Prepublished online Sep. 20, 2006).

* cited by examiner

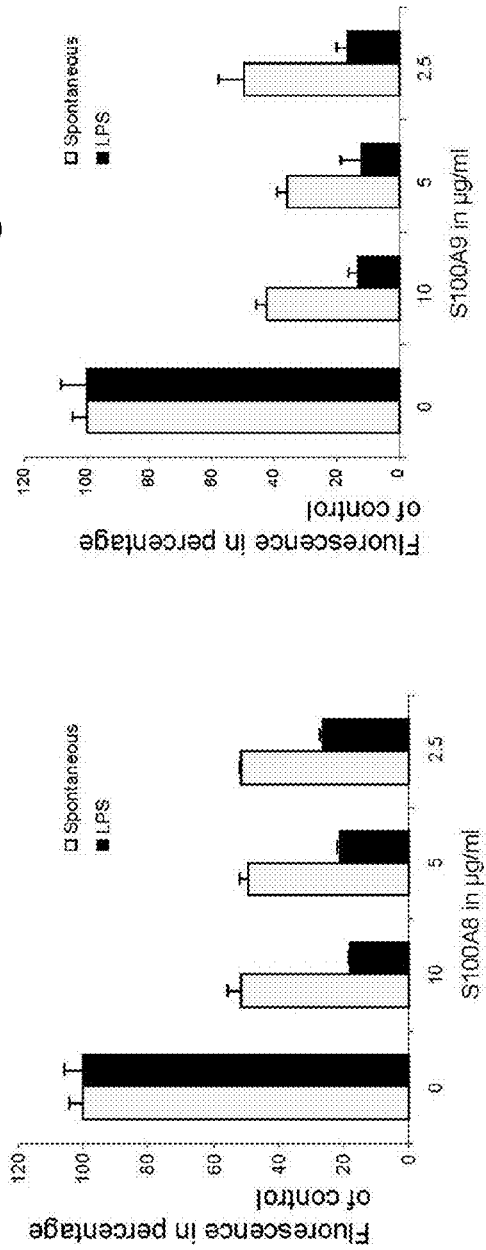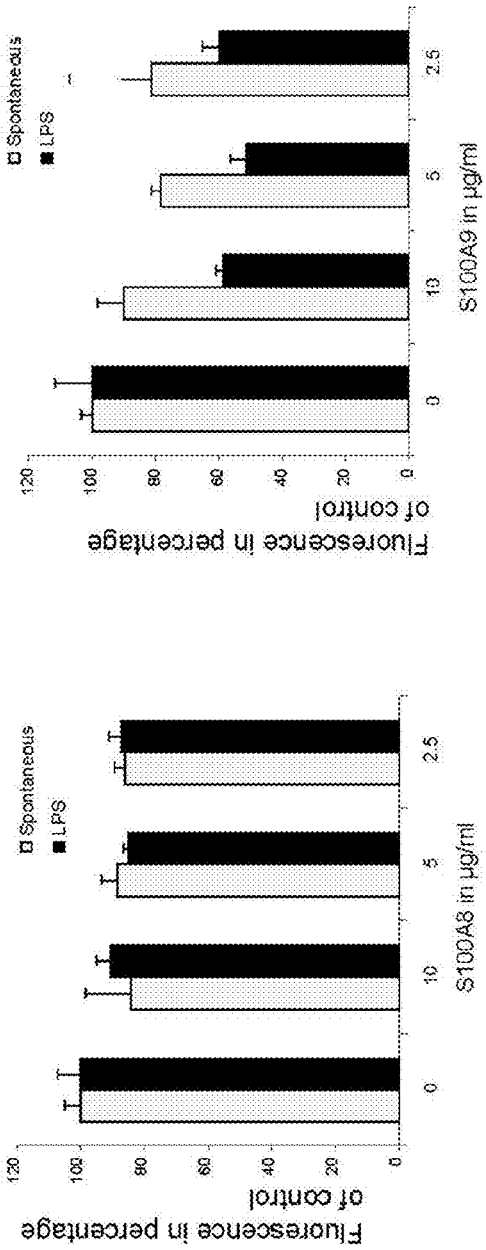

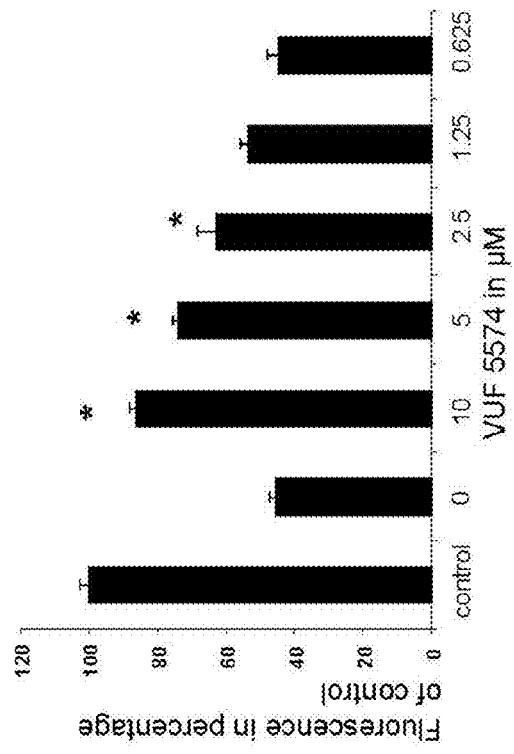
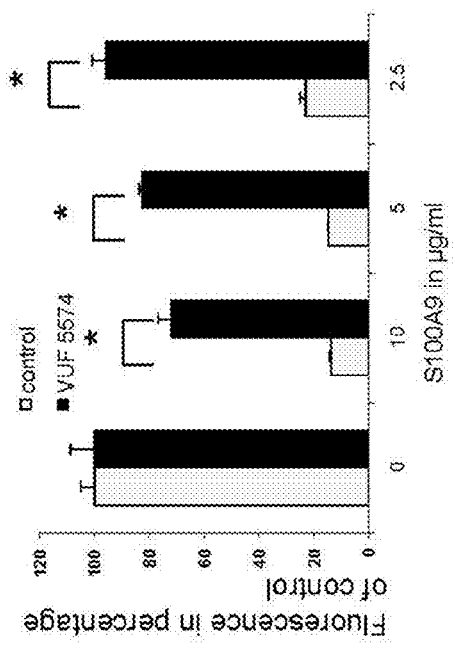
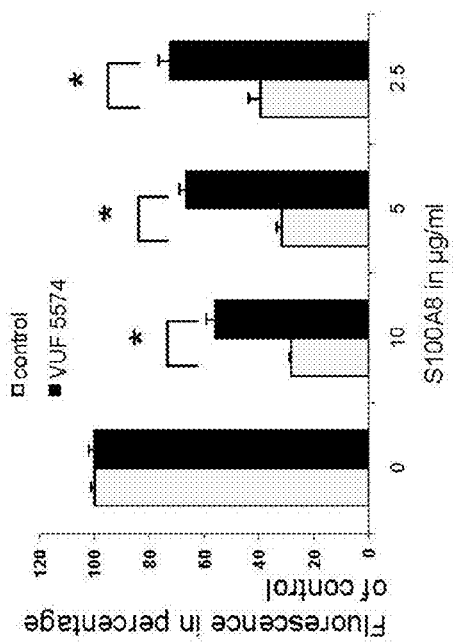
Figure 10A
Figure 10C
Figure 10B

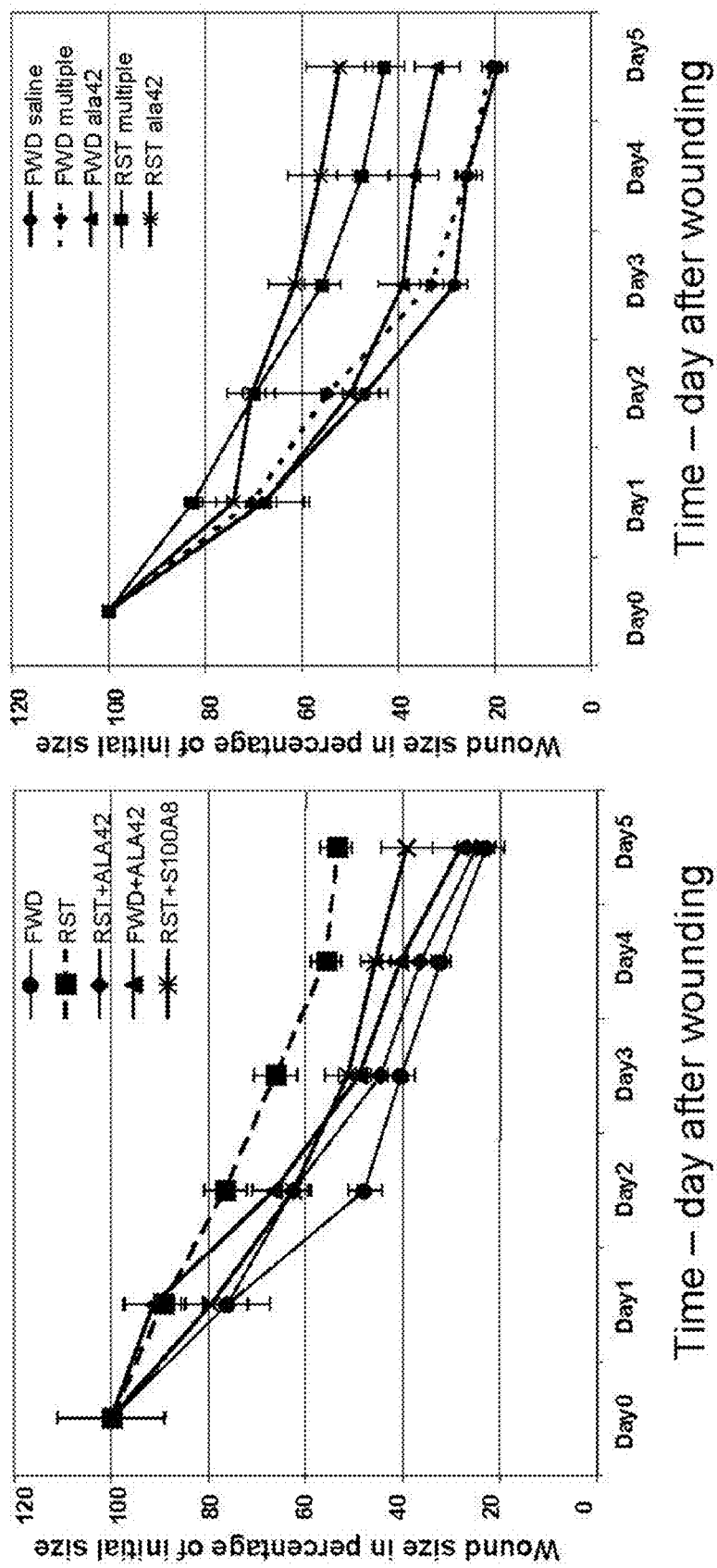

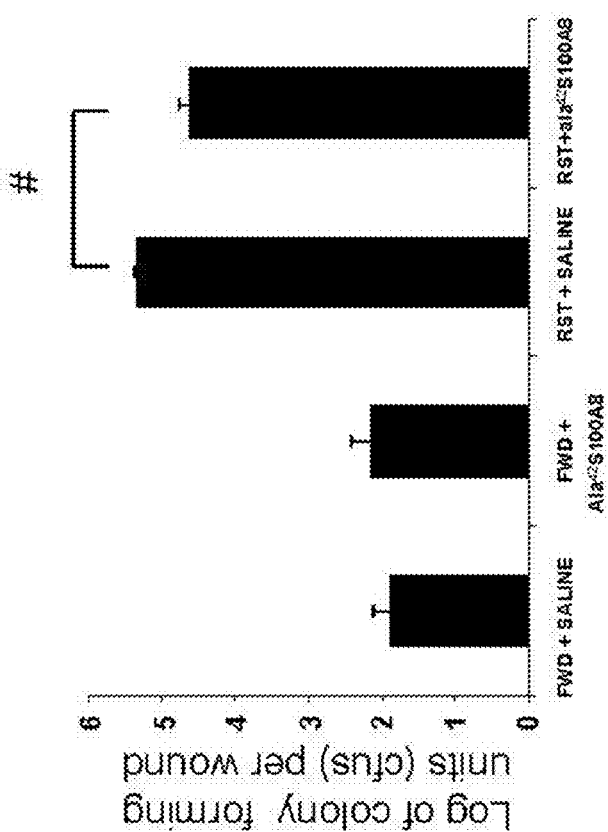
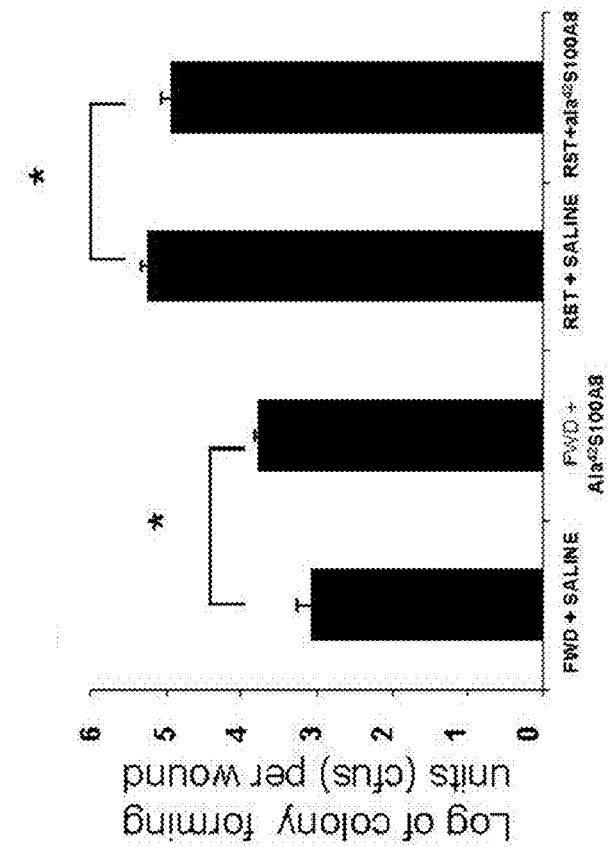
Figure 12A
Figure 12B

```
                       SEQUENCE LISTING

<160> NUMBER OF SEQ ID NOS: 4

<210> SEQ ID NO 1
<211> LENGTH: 282
<212> TYPE: DNA
<213> ORGANISM: Homo sapiens

<400> SEQUENCE: 1
atgttgaccg agctggagaa agccttgaac tctatcatcg acgtctacca caagtactcc      60
ctgataaagg ggaatttcca tgccgtctac agggatgacc tgaagaaatt gctagagacc     120
gagtgtcctc agtatatcag gaaaaagggt gcagacgtct ggttcaaaga gttggatatc     180
aacactgatg gtgcagttaa cttccaggag ttcctcattc tggtgataaa gatgggcgtg     240
gcagcccaca aaaaagcca tgaagaaagc cacaaagagt ag                         282

<210> SEQ ID NO 2
<211> LENGTH: 93
<212> TYPE: PRT
<213> ORGANISM: Homo sapiens

<400> SEQUENCE: 2

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
```

```
              50                  55                  60
Ala Val Asn Phe Gln Glu Phe Leu Ile Leu Val Ile Lys Met Gly Val
 65                  70                  75                  80

Ala Ala His Lys Lys Ser His Glu Glu Ser His Lys Glu
                 85                  90

<210> SEQ ID NO 3
<211> LENGTH: 345
<212> TYPE: DNA
<213> ORGANISM: Homo sapiens

<400> SEQUENCE: 3
atgacttgca aaatgtcgca gctggaacgc aacatagaga ccatcatcaa caccttccac      60
caatactctg tgaagctggg gcacccagac accctgaacc aggggaatt caaagagctg     120 gtgcgaaaag atctgcaaaa ttttctcaag aaggagaata agaatgaaaa ggtcatagaa     180
cacatcatgg aggacctgga cacaaatgca gacaagcagc tgagcttcga ggagttcatc     240
atgctgatgg cgaggctaac ctgggcctcc cacgagaaga tgcacgaggg tgacgagggc     300
cctggccacc accataagcc aggcctcggg gagggcaccc cctaa                     345

<210> SEQ ID NO 4
<211> LENGTH: 114
<212> TYPE: PRT
<213> ORGANISM: Homo sapiens

<400> SEQUENCE: 4

Met Thr Cys Lys Met Ser Gln Leu Glu Arg Asn Ile Glu Thr Ile Ile
 1               5                  10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
            35                  40                  45

Leu Lys Lys Glu Asn Lys Asn Glu Lys Val Ile Glu His Ile Met Glu
 50                  55                  60

Asp Leu Asp Thr Asn Ala Asp Lys Gln Leu Ser Phe Glu Glu Phe Ile
 65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro
```

MYELOID PROTEIN ACTIVATION OF ANTI-INFLAMMATORY AND ANTI-HYPOXIC PATHWAY

CROSS-REFERENCE TO RELATED APPLICATIONS

This application is a Continuation of U.S. application Ser. No. 12/551,225, filed Aug. 31, 2009 now abandoned, which application claims the benefit of U.S. Provisional Application No. 61/093,100, filed Aug. 29, 2008, U.S. Provisional Application No. 61/138,270, filed Dec. 17, 2008, U.S. Provisional Application No. 61/147,599, filed Jan. 27, 2009 and U.S. Provisional Application No. 61/155,208, filed Feb. 25, 2009, all of which are incorporated by reference herein to the extent there is no inconsistency with the present disclosure.

STATEMENT REGARDING FEDERALLY SPONSORED RESEARCH OR DEVELOPMENT

This invention was made with government support under Grant No. NIDCR K22 DE017161 awarded by the National Institutes of Health. The government has certain rights in the invention.

REFERENCE TO SEQUENCE LISTING, A TABLE, OR A COMPUTER PROGRAM LISTING COMPACT DISK APPENDIX

The Sequence Listing submitted herewith is incorporated by reference herein.

BACKGROUND OF THE INVENTION

The present methods relate to treatments for the amelioration of conditions associated with potential oxidative damage, hypoxia, reperfusion injury, ischemic events, systemic infections, as well as treatments for improving patient conditions worsened by psychological stresses.

The infiltration of damaged tissue by polymorphonuclear neutrophilic leukocytes (neutrophils) and their subsequent activation is a crucial for defense against microbial threats. Once recruited during acute inflammation, neutrophils produce and release copious amounts of reactive oxygen species (ROS) which target potential bacterial invaders. A failure in sufficient production of ROS leads to infections as observed in chronic granulomatous disease (CGD), a disease prompted by a deficient oxidase system in neutrophils [1]. Conversely, excess ROS production is associated with conditions such as chronic wounds [2] and cardiovascular diseases [3]. However, tissue damage can trigger deleterious responses from host defenses, leading to still further tissue damage. There is a need for methods and compositions to enhance healing of an accidental or surgical wound and/or to reduce deleterious effects of endogenous cells, factors and systems in response either to an event such as an injury, an ischemic event, reperfusion injury or potential reperfusion injury, an infarction, such as a cardiac or cerebral infarction, reperfusion of an organ associated with a transplant or the effects of physical and/or psychological stress(es).

Calprotectin, a heterocomplex formed by S100A8 and S100A9, which are two calcium binding proteins, represents 40% of neutrophil cytosolic proteins (by weight) [4]. High serum levels of calprotectin are associated with an immune deficiency, together with growth retardation and arthritis [5, 6, 7]. Work done by others and confirmed by this laboratory has demonstrated that calprotectin regulates neutrophil migration [8-10]. It is shown that S100A8 and S100A9 repel neutrophils in-vitro and that S100A8 inhibits the recruitment of neutrophils in-vivo.

Neutrophil functions are not restricted to ROS or cytokine production. Neutrophils produce and release several serine proteases [11]. Those proteases directly contribute to neutrophil microbicidal action [12] and affect a broad range of biological processes from coagulation [13] to inflammation [14]. The mechanisms of the observed effect of neutrophil derived serine proteases on inflammation involve the activation or inhibition of protease-activated receptors (PARs), a G-coupled family of receptor comprising 4 members named PAR-1 to PAR-4. PARs are activated after proteolysis of an N-terminal portion of the receptors which result in the unmasking of a tethered ligand (for review see Ossovskaya et al [15]). The regulation of PARs activity is a complex process in which proteases can either activate or inactivate the receptors. Neutrophil derived serine proteases including PR3, cathepsin G and elastase participate in the regulation of PARs activity [16]. For example, Cathepsin G activates PAR-4 [17]. PAR-4 partakes in the regulation of inflammatory processes [18, 19] including the recruitment and activation of neutrophils.

Neutrophils isolated from healthy volunteers spontaneously release proteases such as elastase and ROS such as superoxide anion [20] in-vitro. Spontaneous activation of neutrophil oxidative metabolism in-vitro has been widely documented [21] [22-24]. The production and release of ROS by neutrophils is dependent on the NADPH oxidase system and it can be accelerated by phorbol 12-myristate 13-acetate (PMA), which activates protein kinase C (PKC) and directly phosphorylates critical subunits of the NADPH oxidase complex [25]. Reports have indicated that exaggerated or reduced rates of spontaneous neutrophil activation are linked to viral [26] or autoimmune conditions [27], implying a physiological function for spontaneous neutrophil activation.

Psychological stress affects physiological functioning both directly via somatic pathways, and indirectly by triggering maladaptive behaviors. Studies have suggested that psychological factors appear to interfere directly with wound healing and closure (Godbout and Glaser, 2006). Marital stress, was associated with a 40% delay in wound healing and a defective immune response (Glaser et al., 1999). Caregivers of patients with Alzheimer's disease who reported emotional conflicts, compared with age-matched non-caregiver controls, also exhibited delays in cutaneous wound healing (Kiecolt-Glaser et al., 1995). A study of oral wounds in dental students revealed that healing proceeded at a 40% slower average rate in oral wounds placed 3 days before examinations, compared with identical wounds placed in the same students during their vacations (Marucha et al., 1998).

Cutaneous wound healing is a multi-step process prone to hypoxia. Conceptually, wound healing can be divided into three sequential but overlapping phases: inflammation, proliferation and remodeling (Thomas et al., 1995). Oxygen metabolism and redox homeostasis are critical in all phases of the healing process. Initially, wounding damages blood vessels and reduces oxygen availability. The early post-wounding acute inflammation phase is characterized by the rapid recruitment and activation of peripheral neutrophils. During their activation neutrophils consume large amount of oxygen to produce antimicrobial reactive oxygen species which profoundly alter the biology of the inflamed tissue. Then the healing process combines an early reduction in blood supply with a substantial increase in oxygen demand, further contributing to potential wound hypoxia.

In the established mouse SKH-1 restraint stress model, psychological stress induces delays in wound closure from day 1 post-wounding. Wound closure is slowed by approximately 30% in mice subjected to stress (Padgett et al., 1998). Stress also results in elevated cortiscosterone levels in the bloodstream (Padgett et al., 1998). Delay in wound closure is associated with disregulated inflammation and defective bacterial clearance. Oxygen metabolism and hypoxia appear to be involved in impaired healing seen in stressed animals. Significantly higher inducible nitric oxide synthase (iNOS) levels are present in wounds of stressed compared with control mice (Gajendrareddy et al., 2005). Hyperoxia resulting from hyperbaric oxygen therapy (HBOT) returns iNOS expression to control levels, and partially or wholly reverses the impairment of wound closure associated with psychological stress (Gajendrareddy et al., 2005).

S100A8 is an oxidation-sensitive anti-inflammatory protein which combines with S100A9 to form the heterocomplex calprotectin. By weight, calprotectin represents 40% of total protein in the neutrophil cytosolic fraction. S100A8 and S100A9 are oxidation sensitive repellent of neutrophils which also inhibit neutrophil chemotaxis toward bacterial products (i.e. formylated peptides) in-vitro (Sroussi et al., 2006; Sroussi et al., 2007). Ala$^{42}$S100A8, an oxidation-resistant analog of S100A8 engineered using site-directed mutagenesis, retains its chemo-repulsive activity under oxidative conditions, which would otherwise inhibit the wild type S100A8 protein. In the rat air-pouch model of acute inflammation, ala$^{42}$S100A8 inhibits the recruitment of neutrophils stimulated by bacterial endotoxins (Sroussi et al., 2006).

Previous work has shown that neutrophil depletion results in an accelerated wound closure (Dovi et al., 2003). While neutrophils play an important function in controlling and eliminating bacterial contamination of the wound, reduced neutrophil recruitment and activation seems to be beneficial for wound closure rates possibly by reducing oxygen demand and wound hypoxia. Accordingly, it is hypothesized that S100A8 protein can ameliorate wound healing in a psychological stressed induced model of impaired wounds. Because of the anti-inflammatory nature of S100A8, a secondary aim of this work was to ascertain that S100A8 would not cause a clinically significant defect in wound bacterial clearance. The effect of wild type and ala$^{42}$S100A8 on wound closure in stressed and non-stressed animals was tested. It was found that ala$^{42}$S100A8 introduced locally immediately after wounding ameliorated the delay in wound closure rates caused by restraint stress. This beneficial effect occurred without negatively impacting in a clinically significant manner bacterial clearance in the wounds.

There is a need in the art for methods to counteract the deleterious effects of hypoxia in tissues and in bodily fluids so that patient condition can be improved, despite the negative effects of infarct, ischemia, psychological and/or physical stress.

BRIEF SUMMARY OF THE INVENTION

The present invention provides treatments for the amelioration of conditions associated with potential oxidative damage, hypoxia, reperfusion, ischemic events, toxic shock, septic shock, systemic infections such as sepsis, especially such an infection with a gram negative microorganism, as well as treatments for improving patient condition aggravated by psychological stresses to which the patient is subject. These treatment methods utilize pharmaceutically acceptable compositions comprising a human S100A8 and/or S100A9 protein, or a mutant human S100A8 or S100A9 protein. In some embodiments, the compositions contain S100A8 and/or S100A9 proteins comprising mutations that inhibit the posttranslational modification comprises conferring oxidation resistance to the protein. In preferred embodiments, the mutation further prevents dimerization of the protein. In an embodiment, the mutation results in an amino acid substitution of a cysteine, a lysine or a methionine residue, provided that the mutation does not destroy the leukocyte-repellent activity of the protein. In a particular embodiment, the amino acid substitution comprises a replacement of cysteine at residue 42 with an alanine in the human S100A8 protein. In another preferred embodiment, the amino acid substitution comprises a replacement of Methionine at one or more of residue 61, residue 81, and residue 83, with an Alanine in the human S100A9 protein.

In addition, the present invention provides methods comprising administering to a patient in need thereof a composition comprising a human S100A8 or S100A9 protein (or mutant protein as discussed herein); advantageously via a systemic administration, for example, via an intravenous administration. Moreover, in some embodiments, the protein comprises at least one mutation inhibiting posttranslational modification of said protein. In some embodiments, a mutation which inhibits posttranslational modification comprises conferring oxidation resistance to the protein. In related embodiments, the mutation further prevents dimerization of the protein. Patients to benefit from such an administration of composition comprising a human S100A8 or S100A9 protein (or mutant protein as discussed herein) include those under psychological and/or physical stress, suffering from reperfusion oxidative damage or subject to reperfusion oxidative damage, an ischemic event, a heart attack, hypoxia or other condition associated with oxidative damage, although the conditions conferring need to a patient are not limited only to those specifically recited conditions or challenges. In a particular embodiment, wound healing is improved in a patient with psychological stress.

In embodiments of the invention, the S100A8 and/or S100A9 protein (or mutant protein as discussed herein) is administered within 0.1 minutes to 24 hours, is within 0.5 min to 6 hours, or within 0.5 min or less up to about 4, or up to 1 hour of an ischemia or an infarct. The method of claim 8, wherein the step of administering is from 0.5 min to 24 hours prior to the physical exertion and up to about 24 hours after the physical exertion. Where the effects of reperfusion are to be ameliorated, administration of the S100A8 and or S100A9 proteins (or variants of either or both proteins as described herein) can be from 4 hours prior to reperfusion up to 24 hours after reperfusion, or it can be simultaneous with reperfusion up to 4 hours after reperfusion, or all ranges between the recited ranges.

In the methods of the present invention, administration can be intravenous, intrasynovial or locally administered, depending on the condition being treated. In any of the present methods, the composition is administered at a dose from about 0.05 to about 100 mg/kg body weight, or from about 0.25 to about 10 mg/kg body weight, or any subranges within either of these recited ranges. In embodiments, the amount administered can be a bolus dose such that the final concentration in the bloodstream is from about 0.1 to about 10 µg/ml, from about 0.05 to about 5 µg/ml, or about 0.10 µg/ml.

BRIEF DESCRIPTION OF THE DRAWINGS

FIGS. 9A-9D illustrate fluorescence emission of neutrophils incubated with DCFH-DA probe during 1 hour alone (spontaneous) or in the presence of LPS 10 µg/ml. S100A8 (FIG. 9A) and S100A9 (FIG. 9B) at various concentrations produced a significantly reduction in the spontaneous and LPS induced oxidative metabolism. The addition of 0.01 mU/ml of human adenosine deaminase 1 (ADA1) caused a substantial reduction in S100A8 (FIG. 9C) and S100A9 (FIG. 9D) anti-oxidative effect. Each point is the mean±SD. This is a representative experiment of at least 3 experiments conducted in quadruplicate.

FIGS. 10A-10C display fluorescence emission of neutrophils incubated with DCFH-DA probe during 1 hour alone, LPS, S100A8, S100A9 and/or VUF5574 (an A3 adenosine antagonist). In FIG. 10A, neutrophils were treated with 2.5 µg/ml S100A8 except for control. VUF 5574 produces a dose sensitive inhibition the anti-oxidative effect of S100A8 on neutrophil spontaneous oxidative metabolism (FIG. 10A). In FIGS. 10B and 10C, S100A8 (FIG. 10B) and S100A9 (FIG. 10C) inhibited the oxidative metabolism of neutrophils exposed to 10 µg/ml LPS. This anti-oxidative effect was countered by 10 µM.

FIGS. 11A-B display wound closure over time as percentage of initial wound size. FIG. 11A: Restraint stress (RST) causes a delay in wound closure form day 1 post wounding when compared to control food and water deprived mice (FWD). Ala42S100A8 (RST-ALA42) reverses the delay in closure caused by restraint stress (RST). # p=0.01, *p=0.000 comparing restraint stress group (RST) to RST+ ala42S100A8. FIG. 11B: FWD and RST multiple referred to groups with daily injection of saline. FWD saline group was injected with saline once only post-wounding. ALA42 referred to groups injected daily with ala42S100A8. Daily application of ala42S100A8 results in no sustained amelioration in wound closure rates but in slower healing in FWD animals. # p=0.012, *p=0.006 comparing FWD multiple (daily saline) to ALA42 (daily injection of ala42S100A8). The data represent mean+/−SEM (n=5 per group) of four (FIG. 11A) and two (FIG. 11B) experiments with similar results.

FIGS. 12A and B show the effects of restraint stress on bacterial clearance in control food and water deprived mice (FWD) and restraint stress mice (RST) at day 1 (FIG. 12A) and day 5 (FIG. 12B) post-wounding. Ala42S100A8 significantly increases bacterial counts in FWD mice at day 1 and decreases bacterial counts at day 1 and 5 in RST mice. Mean+/−SEM. n=5 per group. # P<0.01, *P<0.001 comparing CFU counts from ala42S100A8 treated v. control vehicle (saline) treated wounds.

DETAILED DESCRIPTION OF THE INVENTION

Figure 1B:
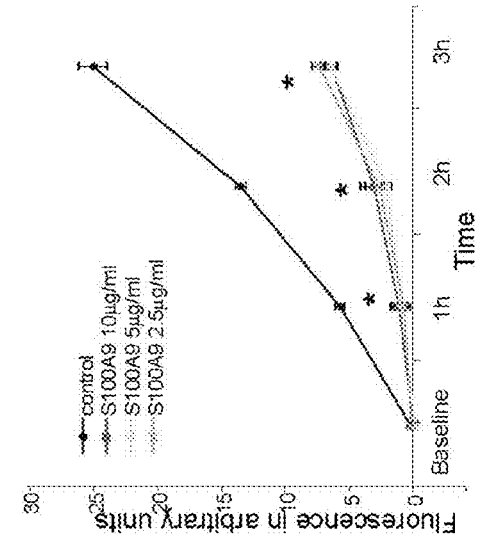
FIGS. 1A-1C show dose dependence of fluorescence emission of neutrophils incubated with DCFH-DA probe and various concentration of S100A8 (FIG. 1A), S100A9 (FIG. 1B) and calprotectin (FIG. 1C) (equivalent weight concentration of both proteins). At 1 h time point, S100A8, S100A9 and calprotectin significantly inhibited oxidative metabolism at all concentrations tested *P<0.05 compared to control. Each point is the mean±SD. This is a representative experiment of at least 4 experiments conducted in triplicate or quadruplicate.

To facilitate an understanding of the present invention, a number of terms and phrases are defined below:

The term "gene" refers to a nucleic acid (e.g., DNA) sequence that comprises coding sequences necessary for the production of a polypeptide or precursor or RNA encoding human S100A8 and/or S100A9. The polypeptide can be encoded by a full length coding sequence or by any portion of the coding sequence so long as the desired activity or functional properties (e.g., enzymatic activity, ligand binding, signal transduction, etc.) of the full-length or fragment is retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

In particular, the term "S100A8 gene" refers to the full-length S100A8 nucleotide sequence (e.g., SEQ ID NO:1). However, it is also intended that the term encompass fragments of the S100A8 nucleotide sequence, as well as other domains (e.g., functional domains) within the full-length S100A8 nucleotide sequence. For example, the term encompasses nucleic acid sequences that are from 50%, 60%, 70%, 80%, 90%, to 95% or more identical (i.e., including all ranges and all integer percents from 50 to 100% identical) in amino acid sequence to SEQ ID NO:1. The term also encompasses nucleic acid sequences that encode an S100A8 protein (e.g., SEQ ID NO:2) and sequences that are from 50%, 60%, 70%, 80%, 90%, to 95% or more (i.e., including all ranges and all integer percents from 50 to 100% identical) identical to SEQ ID NO:2. In each case, the S100A8 sequences preferably encode a protein that confers the beneficial effects of S100A8 with respect to reducing oxidative damage and stimulating wound healing, especially in a patient suffering from an infarction, an ischemic event or psychological stresses. Furthermore, the terms "S100A8 gene," "S100A8 nucleotide sequence," and "S100A8 polynucleotide sequence" encompass DNA, cDNA, and RNA sequences.

The term "plasmid" as used herein, refers to a small, independently replicating, piece of DNA. Similarly, the term "naked plasmid" refers to plasmid DNA devoid of extraneous material typically used to affect transfection. As used herein, a "naked plasmid" refers to a plasmid substantially free of calcium-phosphate, DEAE-dextran, liposomes, and/or polyamines.] As used herein, the term "purified" refers to molecules (especially polypeptides) that are removed from their natural environment, isolated or separated. "Substantially purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA. These terms are not intended to encompass entirely natural products, where there has been no human-directed input of component sequences or starting sequence or where humans have not selected for a particular genetic outcome.

The term "fusion protein" as used herein refers to a protein formed by expression of a hybrid gene made by combining two gene sequences. Typically this is accomplished by cloning a cDNA into an expression vector in frame with an existing gene. The fusion partner may act as a reporter (e.g., n-gal) or may provide a tool for isolation purposes (e.g., GST and affinity chromatography).

Suitable systems for production of recombinant proteins include but are not limited to prokaryotic (e.g., *Escherichia coli*), yeast (e.g., *Saccharomyces cerevisiae*), insect (e.g., baculovirus), mammalian (e.g., Chinese hamster ovary), plant (e.g., safflower), and cell-free systems (e.g., rabbit reticulocyte).

As used herein, the term "coding region" refers to the nucleotide sequences that encode the amino acid sequences found in the nascent polypeptide as a result of translation of an mRNA molecule. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

Where amino acid sequence is recited herein to refer to an amino acid sequence of a naturally occurring protein molecule, "amino acid sequence" and like terms, such as "polypeptide" or "protein," are not meant to limit the amino acid sequence to the complete, native amino acid sequence associated with the recited protein molecule.

The term "wild-type" refers to a gene or gene product that has the characteristics of that gene or gene product when isolated from a naturally occurring source. A wild type gene is that which is most frequently observed in a population and is thus arbitrarily designed the "normal" or "wild-type" form of the gene.

As used herein, the terms "mutant," "polymorphism," and "variant," in reference to a gene or gene product, refer to alterations in sequence and/or functional properties (i.e., different characteristics) when compared to the wild-type gene or parental gene product. In some preferred embodiments, the term mutant refers to a gene or gene product that differs from a parental gene or gene product as a result of mutation. It is noted that naturally occurring and induced mutants can be isolated; these are identified by the fact that they have altered characteristics when compared to the wild-type gene or parental gene product. In addition, mutant genes can be artificially (e.g., site-directed mutagenesis) or synthetically produced in the laboratory.

The term "mutation" refers to a change in the number, arrangement, or molecular sequence of nucleotides in a genetic sequence. In other embodiments "mutation" refers to a change in number, arrangement, or a specified amino acid sequence of a peptide or a protein.

As used herein in reference to a protein, the term "modified" refers to proteins with structural changes including primary, secondary, tertiary, etc. changes. Thus, the term "modified" encompasses but is not limited to amino acid deletions, insertions and substitutions (e.g., as a result of mutation), as well as post-translational modifications such as glycosylation, acylation, limited proteolysis, phosphorylation, isoprenylation and oxidation. In addition, the term modified encompasses the replacement of a native amino acid with a non-standard residue including but not limited to acetamidomethyl, aminohexanoic acid, aminoisobutyric acid, beta-alanine, cyclohexylalanine, D-cyclohexylalanine, e-acetyl lysine, gamma aminobutyric acid, hydroxyproline, nitro-arginine, nitro-phenylalanine, nitro-tyrosine, norleucine, norvaline, octahydroindole carboxylate, ornithine, penicillamine, phenylglycine, phosphoserine, phosphothreonine, phosphotyrosine, pyroglutamate, and tetrahydroisoquinoline.

The terms "S100A8," "cystic fibrosis antigen," "calprotectin," "calgranulin A," "L1 light chain," "CP-10" and "MCPS," as used herein refer to a human S100A8 gene (e.g., *Homo sapiens*—GENBANK Accession No. NM 002964) and its gene product (GENBANK Accession No. NP 02955.2), including wild type and mutant products. Human S100A8 variants, which differ from the wild type S100A8 sequences in fewer than 1% of the residues, are also suitable for use in the methods and compositions of the present invention, provided that the beneficial effect of the wild-type protein is retained. See also SEQ ID NOs: 1 and 2.

As used herein, the terms "S100A9," "calgranulin B," "L1 heavy chain," and "MCP 14" refer to a human S100A9 gene (e.g., *Homo sapiens*—GENBANK Accession No. NM 002965) and its gene product (GENBANK Accession No. NP 002956.1), including wild type and mutant products. See also SEQ ID NOs: 3 and 4. Human S100A9 variants, which differ from the wild type S100A9 sequences in fewer than 1% of the residues, are also suitable for use in the methods and compositions of the present invention. For example, methionines at positions 63 and/or 83 can be substituted.

As used herein, the terms "complementary" and "complementarity" refer to polynucleotides related by base-pairing rules. For example, for the sequence "5'-AGT-3'," the complementary sequence is "3'-TCA-5'."

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, e.g., Winter and Milstein, Nature, 349, 293-299, 1991). As used herein, the term "antibody" encompasses recombinantly prepared, and modified antibodies and antigen-binding fragments thereof, such as chimeric antibodies, humanized antibodies, multifunctional antibodies, bispecific or oligo-specific antibodies, single-stranded antibodies and F(ab) or $Fab_2$ fragments. The term "reactive" in used in reference to an antibody indicates that the antibody is capable of binding an antigen of interest. For example, an S100A8-reactive antibody is an antibody, which binds to S100A8 or to a fragment of S100A8.

The term "portion" when used in reference to a nucleotide sequence refers to fragments of that sequence, which range in size from 10 contiguous nucleotides to the entire nucleotide sequence minus one nucleotide.

As used herein, the term "biologically active" refers to a molecule having structural, regulatory and or biochemical functions of a wild type homeobox molecule. In some instances, the biologically active molecule is a homolog of a mammalian homeobox molecule, while in other instance the biologically active molecule is a portion of a mammalian homeobox molecule. Other biologically active molecules, which find use in the compositions and methods of the present invention include but are not limited to mutant (e.g. variants with at least one deletion, insertion or substitution) mammalian S100 molecules. Biological activity is determined for example, by restoration or introduction of S100 (e.g., S100A9 or S100A8) activity in cells which lack S100 activity, through transfection of the cells with a S100 expression vector containing a S100 gene, derivative thereof, or portion thereof. Methods useful for assessing S100A8 and S100A9 activity include but are not limited to transwell migration assays, as well known to the art.

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer [ed.], Biochemistry, pg. 17-21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.).

As used herein the term "animal" refers to any member of the kingdom Animally, which includes living things, which have cells differing from plant cells with regard to the absence of a cell wall and chlorophyll and the capacity for spontaneous movement. Preferred embodiments of the present invention are primarily directed to vertebrate (backbone or notochord) members of the animal kingdom.

The terms "patient" and "subject" refer to a mammal or an animal who is a candidate for (in need of) receiving medical treatment.

The term "control" refers to subjects or samples which provide a basis for comparison for experimental subjects or samples. For instance, the use of control subjects or samples permits determinations to be made regarding the efficacy of experimental procedures.

As used herein, the terms "gene transfer" and "transfer of genetic information" refer to the process of moving a gene or genes from one place to another. In preferred embodiments of the present invention, the term "gene transfer" refers to the transfer of a polynucleotide to cells and/or tissues of an animal to achieve a therapeutic effect. In some embodiments, the polynucleotide may be in the form of a plasmid, a gene fragment or an oligonucleotide. In some embodiments, "gene transfer" is temporary or transient, in other embodiments "gene transfer" is sustained, and in still further embodiments, the gene transfer is long-lived, permanent or stable. As used herein, "gene transfer" may affect the transfection of cells and/or tissues. The term "transfection" refers to the introduction of foreign DNA into eukaryotic cells.

As used herein, the terms "localized" and "local" refer to the involvement of a limited area. Thus, in contrast to "systemic" treatment, in which the entire body is involved, usually through the vascular and/or lymph systems, localized treatment involves the treatment of a specific, limited area.

As used herein, the terms "systemically active drug" and "systemically active agent" are used broadly to indicate a substance or composition that will produce a pharmacologic response at a site remote from the point of application. In an embodiment, the S100A8 and/or S100A9 is systemically active to enhance wound healing in a stressed patient and/or to protect a patient from the deleterious effects of ischemic events or infarcts or reperfusion.

The terms "sample" and "specimen" are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid, semen, saliva, and wound exudates, as well as solid tissue. However, these examples are not to be construed as limiting the sample types applicable to the present invention.

As used herein, the term "oxidation resistance" refers to the ability to resist the loss of electrons from oxidation.

The term "dimerization" and alternatively "dimerism, as used herein refers to the ability to form a structure from the association of two subunits.

As used herein, the term "amino acid substitution" refers to an act, process, or result of substituting amino acids, especially via spontaneously selected or directed changes in coding sequence in nucleic acid encoding an S100A8 and/or S100A9 protein.

The term "leukocyte" as used herein, refers to cells called white blood cells, that help the body fight infections and other diseases, and include for instance granulocytes (e.g., neutrophils, eosinophils, basophils), monocytes, and lymphocytes (e.g., B cells, T cells, natural killer cells).

As used herein, the term "monocyte" refers to a mononuclear phagocyte circulating in blood that will later emigrate into tissue and differentiate into a macrophage.

The terms "neutrophil," and "major circulating phagocytic polymorphonuclear granulocyte," refer to a type of white blood cell characterized by secondary granules that stain pink with Wright or Giemsa stains and which constitute approximately 60% of the blood in a healthy individual.

As used herein, the term "chemokine" refers to soluble factors (e.g., cytokines) that have the ability to selectively induce chemotaxis and activation of leukocytes. They also trigger integrin-mediated leukocyte activation, and attract leukocytes to places where they are needed (e.g., sites of inflammation or infection). Currently, the chemokine superfamily is separated into three distinct subfamilies called Alpha (or C-X-C), Beta (C-C), and Gamma (C). These designations are based upon the positioning of their cysteine residues. The Alpha chemokines have a single amino acid inserted between the first and second of their four cysteine residues, hence C-X-C, whereas these cysteines are not separated in the Beta group, hence C-C, while the gamma (C) chemokines have only one pair of cysteines.

The term "chemotaxis" as used herein refers to a response of motile cells in which the direction of movement is toward the direction of a gradient (e.g., up) of a diffusible substance. This differs from "chemokinesis" in that the gradient alters probability of motion in one direction only, rather than rate or frequency of random motion.

As used herein, the terms "fugetaxis" and "anti-chemotaxis" refer to a response of motile cells in which the direction of movement is away from the gradient (e.g., down) of a diffusible substance.

The term "inflammation" as used herein, refers to the tissue response to trauma, characterized by increased blood flow and entry of leukocytes into the tissues, resulting in swelling, redness, elevated temperature and pain.

As used herein, the term "symptom" refers to any subjective evidence of disease or of a patient's condition (e.g., a change in a patient's condition indicative of some bodily or mental state). For instance, the phrase "symptoms of inflammation" in the context of inflammatory bowel disease (IBD) is herein defined to include, but is not limited to symptoms such abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g., anemia) or a test that detects the presence of blood (e.g., rectal bleeding).

Similarly, the phrase "under conditions such that the symptoms are reduced" relates to effects including, but not limited to, a detectable impact on the rate of recovery from disease (e.g., rate of weight gain), or the reduction of at least one of the following symptoms: abdominal pain, diarrhea, rectal bleeding, weight loss, fever, loss of appetite, dehydration, anemia, distention, fibrosis, inflamed intestines and malnutrition.

As used herein, the term "allergy" refers to a group of symptoms precipitated by an immune response to substances not typically triggering in an immune response in most individuals. Specific symptoms depend on the specific allergen (inciting substance), the body part exposed, and individual variation in immune responsiveness.

As used herein, the term "asthma" refers to a condition characterized by inflammatory constriction or congestion of the bronchial tree, causing wheezing, coughing and difficult breathing. Alternatively known as reactive airway disease.

As used herein, the term "arthritis" refers to an inflammatory condition that affects joints, which may be caused by, but not limited to, trauma (including long-term wear and tear), infection, or autoimmune responses.

As used herein, the term "atherosclerosis" refers to a form of arteriosclerosis in which fatty deposits form on the inner walls of arteries and block the flow of blood.

As used herein, the term "autoimmune disease" refers to the pathological result when the immune system destructively attacks the body's own organs and tissues. An autoimmune disease may be the result of an amplification of naturally occurring reactivity that causes structural or functional pathology. The term autoimmune disease encompasses but is not limited to arthritis, diabetes, lupus, and multiple sclerosis.

As used herein, the term "infection" refers to invasion and reproduction of microorganisms in the body, which may be clinically undetectable or may result in tissue damage.

As used herein, the term "injury" refers to hurt, damage, or loss sustained of body tissue.

As used herein, the term "ischemia" refers to an interruption in blood flow (and accordingly, oxygen) to one or more tissues or portions of organs or the like.

As used herein, the term "heart attack" refers to an event such as a myocardial infarction, in which there is potential tissue damage due to an in blood flow (and accordingly, oxygen).

As used herein, the term "sepsis" and "systemic infection" refers to a systemic infection or infection of the bloodstream and/or lymph system.

As used herein, the term "pain" refers to the usually localized physical suffering associated with bodily disorder (as in a disease or an injury). In particular, pain is a basic bodily sensation induced by a noxious stimulus, received by naked nerve endings, and characterized by physical discomfort (as pricking, throbbing, or aching).

As used herein, the term "heat" refers to becoming warm or hot (increased temperature). The term "redness" refers to the quality or state of being red. The term "swelling" refers to an expansion (as in size, volume, or numbers) beyond a normal or original limit. For example, tissue may become distended or puffed up, to form a bulge or rounded elevation due in part of leukocyte migration to the site of injury or tissue damage.

Psychological stress is known to slow healing of wounds in humans and animals (See, for example Padgett et al. (1998) Brain Behav. Immun. 12(1):64-73). In animals, hyperbaric oxygen restored the healing ability nearly to control levels in an animal model (Gajendrareddy et al. (2005) Brain Behav. Immun. 19(3):217-222).

S100 is a large evolutionarily-conserved subfamily of EF-hand calcium binding proteins. The basic structure of S100 proteins is as dimers, since S100 monomers are unstable. S100A8 and S100A9 also form calcium-dependent heterodimers and higher order species. The heterodimers are noncovalently bonded and are preferentially formed in solution over homodimers of each S100 protein. However upon oxidation, S100A8 preferentially homodimerizes following the formation of an intermolecular disulfide bridge between conserved cysteine residues (Harrison et al., J Biol Chem, 274:8561-8569, 1999).

S100A8 is also known as cystic fibrosis antigen (in complex with S100A9), p 23 (in complex with S100A9), calprotectin (in complex with S100A9), calgranulin A, L1 light chain, CP-10 and MCP-8. S100A9 is also known as calgranulin B, L1 heavy chain, and MCP-14. In addition, the complex of S100A8 and S100A9 was shown to bind to arachidonic acid, the metabolites of which are involved in inflammation (Klempt et al., FEBS Lett, 408:81-84, 1997).

S100A8 and S100A9 lack a leader sequence or a transmembrane region and are secreted by a novel secretory pathway (Rammes et al., J Biol Chem, 272:9496-9502, 1997). These proteins are expressed in cells of the myeloid lineage and may represent up to 45% of the total cytosolic protein content of neutrophils (Edgeworth et al., J Biol Chem, 266: 7706-7713, 1991). S100A8 and S100A9 are also produced in peripheral monocytes (PM) and tissues macrophages, as well as in epithelial cells under inflammatory conditions such as psoriasis (Nagpal et al., Cell Growth Differ, 7:1783-1791, 1996). Moreover, normal buccal mucosal epithelial cells express S100A8 and S100A9 constitutively at low levels (Wilkinson et al., J Cell Sci, 91:221-230, 1988), whereas keratinized epithelium expresses the two proteins under conditions of stress (Marionnet et al., J Invest Dermatol, 121: 1447-1458, 2003). S100A8 and S100A9 are also detectable in the circulation.

S100A8 and S100A9 exhibit chemoattractant properties based on several lines of evidence (Kerkhoff et al., Biochim Biophys Acta, 1448:200-211, 1998; and Passey et al., J Leukoc Biol, 66:549-556, 1999). The murine homologue of S100A8 is a strong chemoattractant for peripheral monocytes (PM) and neutrophils at an extremely low concentration ($10^{-13}$ M) (Lackmann et al., J Immunol, 150:2981-2991, 1993). In addition, bovine S100A2 and S100A7 (psoriasin) are chemotactic for guinea pig eosinophils and for CD4+ T lymphocytes and neutrophils, respectively (Komada et al., Biochem Biophys Res Commun, 220:871-874, 1996; and Jinquan et al., J Invest Dermatol, 107:5-10, 1996).

Understanding the functions of human S100A8 and S100 A9 is important because they are detected at a high level in a wide variety of inflammatory conditions (Gabrielsen et al., J Am Acad Dermatol, 15:173-179, 1986) both locally in epithelium and in the circulation (Lugering et al., Clin Exp Immunol, 101:249-253, 1995; Lugering et al., Digestion, 56:406-414, 1995; and Muller et al., J Acquir Immune Defic Syndr, 7:931-939, 1994). However, studies of the chemoattractant properties of human S100A8 and S100A9 have yielded variable results. While some investigators have reported chemotactic activity for S100A8 (Ryckman et al., J Immunol, 170:3233-3242, 2003), others have been unable to demonstrate a similar effect. Some have attributed this discrepancy to the susceptibility of the proteins to oxidation (Roth et al., J Immunol, 171:5651, 2003), but this discrepancy could also be attributed differences in methodology used to produce and assay the proteins.

Oxidation regulates the anti-inflammatory activity of S100A8. In addition, as shown herein, the Cys→Ala S100A8 mutant protein acts as an inhibitor of LPS activation of the inflammatory process in vivo and it reverses the negative effects of psychological stress on bacterial clearance and on wound healing. In addition, the residues which confer oxidative sensitivity to S100A8 and S100A9 are necessary for the anti-fungal activity of calprotectin. Oxidized S100A8/A9 proteins have antimicrobial activity; by contrast, non-oxidized calprotectin has anti-inflammatory activity.

In the present disclosure, the following abbreviations apply: eq (equivalents); M (Molar); mM (millimolar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cc (cubic centimeters); cm (centimeters); mm (millimeters); μm (micrometers); nm (nanometers); ° C. (degrees Centigrade); by (base pair); kb (kilobase); WT (wild type); PM (peripheral monocytes); MCP1 (monocyte chemotactic protein); IL-8 (interleukin-8); PCR (polymerase chain reaction); Ab (antibody); mAb (monoclonal antibody); BME (2-mercaptoethanol) SDS (sodium dodecyl sulfate); $MgCl_2$ (magnesium chloride); NaCl (sodium chloride); EDTA (ethylene diamine tetraacetic acid); DEPC (diethyl pyrocarbonate); SSC (salt sodium citrate); BSA (bovine serum albumin); FCS (fetal calf serum); PBS (phosphate buffered saline); Tris (tris(hydroxymethyl) aminomethane); $H_2O$ (water); IgG (immunoglobulin); Sigma (Sigma Chemical Co., St. Louis, Mo.).

Figure 1A:
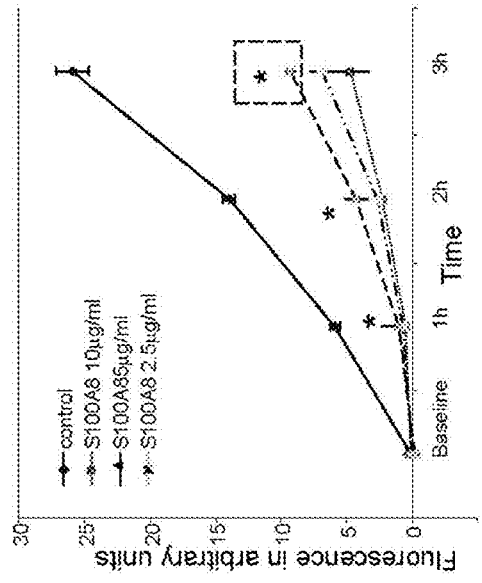
Figure 1C:
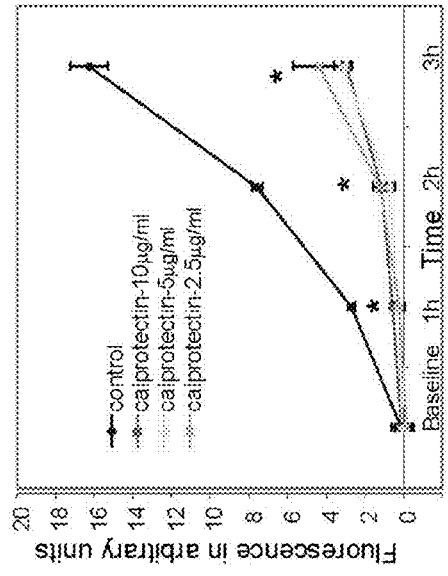

S100A8 and S100A9 were demonstrated to decrease spontaneous oxidative activation of neutrophils. The experimental conditions in which peripheral neutrophils were tested were such that incubation resulted in the relatively slow oxidation of the dichlorofluorescein-diacetate (DCFH-DA) probe in the absence of any further stimuli. This process was followed over time in the presence and absence of different concentrations of S100A8, S100A9 and with a mixture of both (at a 1:1 weight ratio) referred to as calprotectin (FIG. 1). S100A8 and S100A9 together and each alone reduced the rate at which spontaneous oxidation of the DCFH-DA probe occurred in a dose dependent manner (FIG. 1A-C) at concentrations ranging from 2.5 to 10 μg/ml of protein (p values range from <0.001 to <0.05).

Figure 2A:
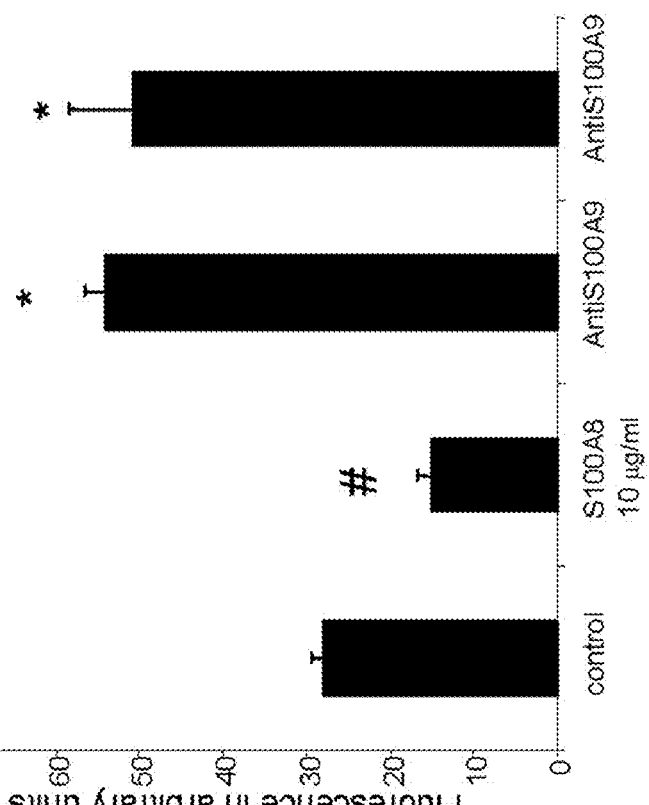
FIGS. 2A-2B show fluorescence emission of neutrophils incubated with DCFH-DA probe for 3 hour in the presence of 5 µg/ml S100A8 or S100A9 which were heat inactivated S100A8 (boiled for 5 minutes) (FIG. 2A) or antibodies directed against S100A8 or S100A9 (FIG. 2B) at a concentration of 1 µg/ml each. *=P<0.05 compared to control. The data represents the mean±SD. This is a representative experiment of 3 experiments conducted in triplicate.

In order to rule out the possibility that S100 proteins reduced the oxidation of the DCFH probe in a non-specific manner, additional control experiments were conducted. First, the S100 proteins were boiled and tested for their anti-oxidative function. Whereas S100A8 at concentrations of 5, 2.5 and 1.25 μg/ml inhibited the oxidative activation of neutrophils (p<0.05), the same concentrations of S100A8 did not significantly affect the neutrophils when the protein was first boiled (similar data were obtained with S100A9) (FIG. 2A).

Figure 2B:
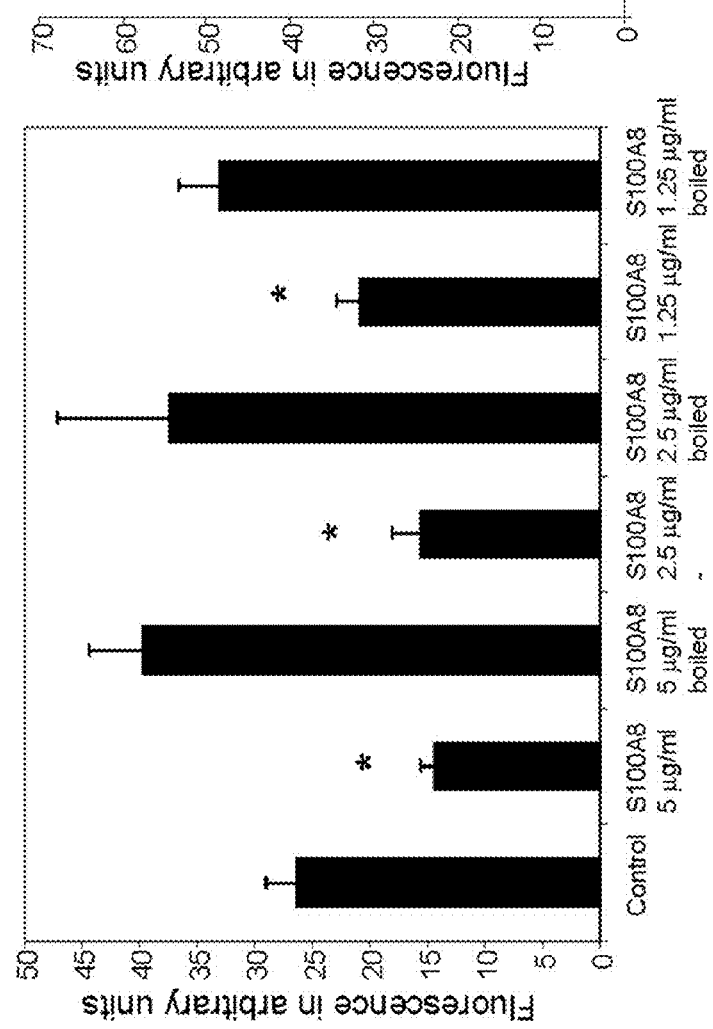

Secondly, because neutrophils produce and release S100A8 and S100A9 [31], the effect of blocking the activity of endogenous S100A8/S100A9 on the oxidative metabolism of neutrophils was tested. The data indicated that antibodies to S100A8 or S100A9 caused an increase in the rate of DCFH oxidation, an effect opposite to the effect observed with the addition of extrinsic S100A8 or S100A9 (FIG. 2B). Isotypic control antibodies had no measurable effect on DCFH oxidation (data not shown). Together those two controls supported the hypothesis that S100A8 and S100A9 had a specific inhibitory effect on neutrophil oxidative metabolism and that intrinsic S100A8 and S100A9 had a constitutive activity during the conduct of the DCFH oxidation assays.

Figure 3:
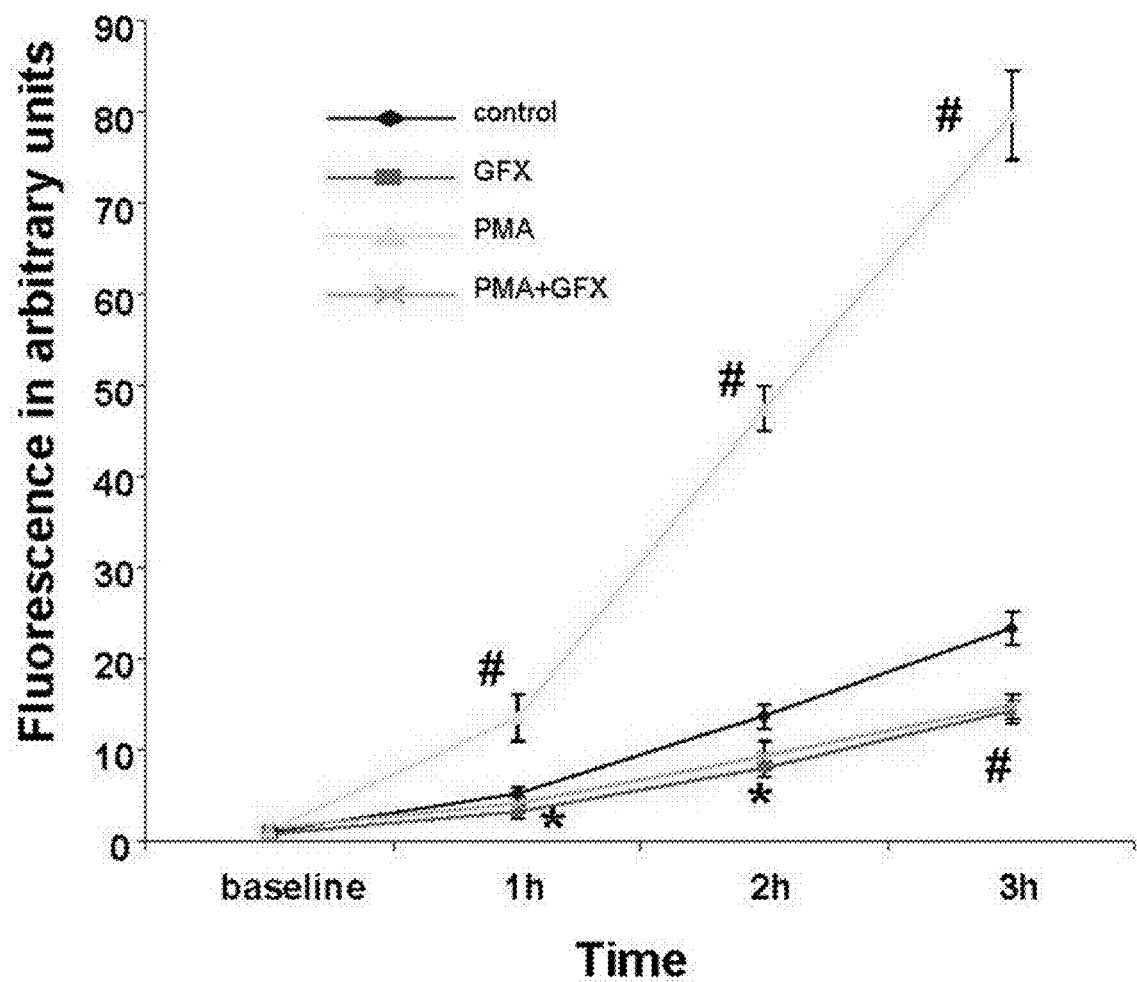
FIG. 3 shows fluorescence emission results of neutrophils incubated with DCFH-DA probe in the presence of 1 µM PMA. 5 µM GFX caused a significant decrease in the spontaneous and the PMA induced oxidation of the DCFH-DA probe.

The spontaneous activation of neutrophil oxidative metabolism was inhibited by GFX, a PKC inhibitor. While spontaneous oxidation of the DCFH probe by neutrophils in this assay was extensively documented, phorbol myristate acetate (PMA), a protein kinase C (PKC) activator that directly phosphorylates and activates the NADPH oxidase (25) significantly accelerated the rate of DCFH oxidation. GFX (Bisindolylmaleimide I) a broad PKC inhibitor significantly inhibited both the PMA induced and the spontaneous activation of neutrophils oxidative metabolism (FIG. 3). In the presence of GFX, both the spontaneous and the PMA triggered oxidative metabolism were reduced significantly below control levels. This would indicate that the spontaneous activation of neutrophils, similarly to the PMA activation, was dependent on PKC activity, supporting the argument that the spontaneous activation was a genuine activation of neutrophil oxidative mechanism (25).

Figure 4B:
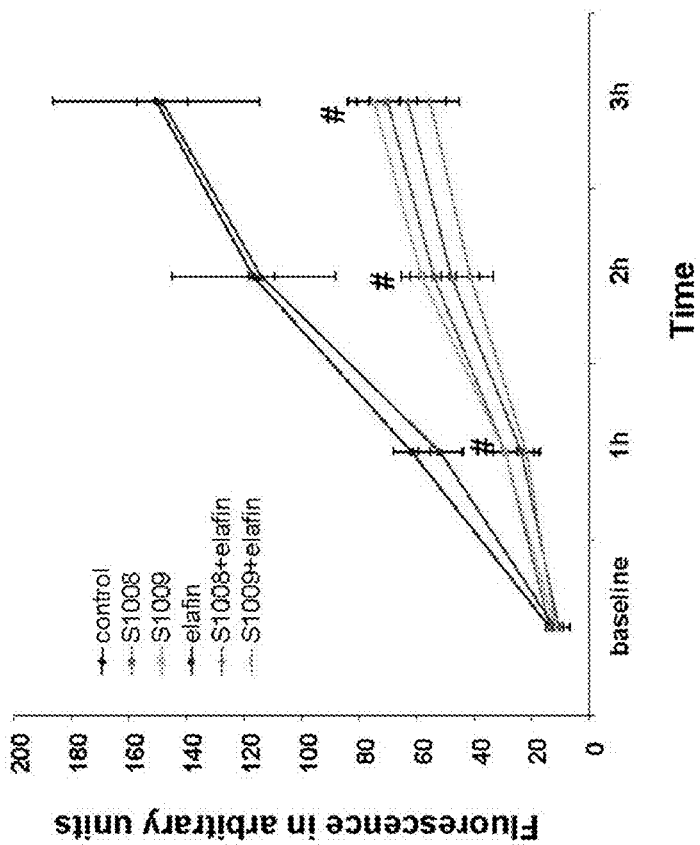
FIGS. 4A-4B show time course results of fluorescence emission of neutrophils incubated with DCFH-DA probe in the presence 10 mg/ml S100A8, 10 mg/ml S100A9 and/or 10 mM α1 antichymotrypsin (FIG. 4A) and 10 mM elafin (FIG. 4B). From 1 hour time point (1 h) S100A8, S100A9 and α1 antichymotrypsin caused a significant and cumulative reduction in the rate of DCFH oxidation. Conversely, elafin had no effect on DCFH oxidation. # P<0.01 compared to control. The data represents the mean±SD. This is a representative experiment of 3 experiments conducted in triplicate or quadruplicate.
Figure 4A:
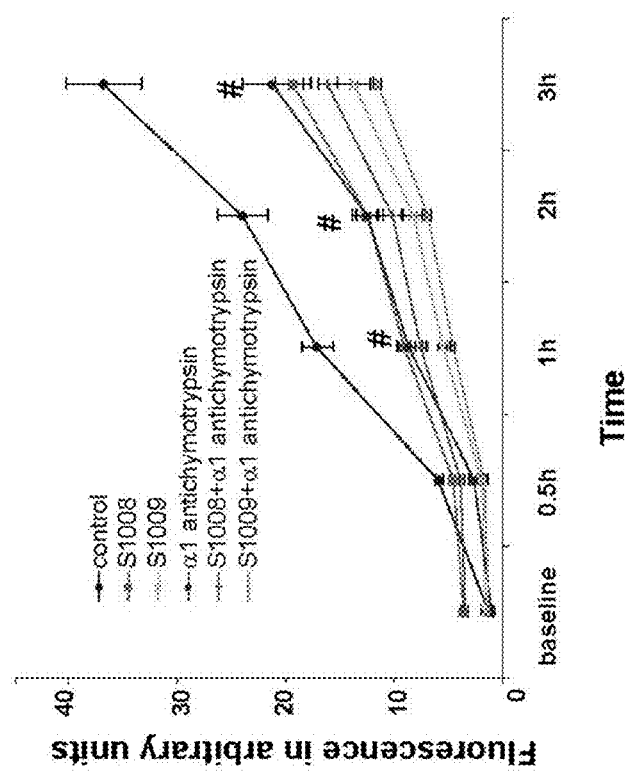

Spontaneous neutrophil oxidative metabolism was shown to be dependent on proteolytic activity. In the next set of experiments, neutrophils were treated with a cocktail of protease inhibitors (complete Mini-Roche). This treatment resulted in a strong inhibition of spontaneous neutrophil oxidative metabolism in a magnitude similar to what was observed with 10 μM S100A8. In order to further characterize which neutrophil protease was involved in the process of spontaneous oxidative activity, the effect of two selective serine protease inhibitors: Elafin and α1 antichymotrypsin was tested. Elafin is an inhibitor of PR3 and elastase whereas α1 antichymotrypsin inhibits cathepsin G [11]. The data indicated that incubating neutrophils with α1 antichymotrypsin (FIG. 4A), but not elafin (4B) caused a marked and significant reduction in the oxidation of the DCFH probe. This finding implicates cathepsin G and not PR3 or elastase in the spontaneous activation of neutrophil oxidative metabolism. α1 antichymotrypsin and S100 proteins had a cumulative effect which was not observed when elafin and S100 proteins were added together.

Figure 5:
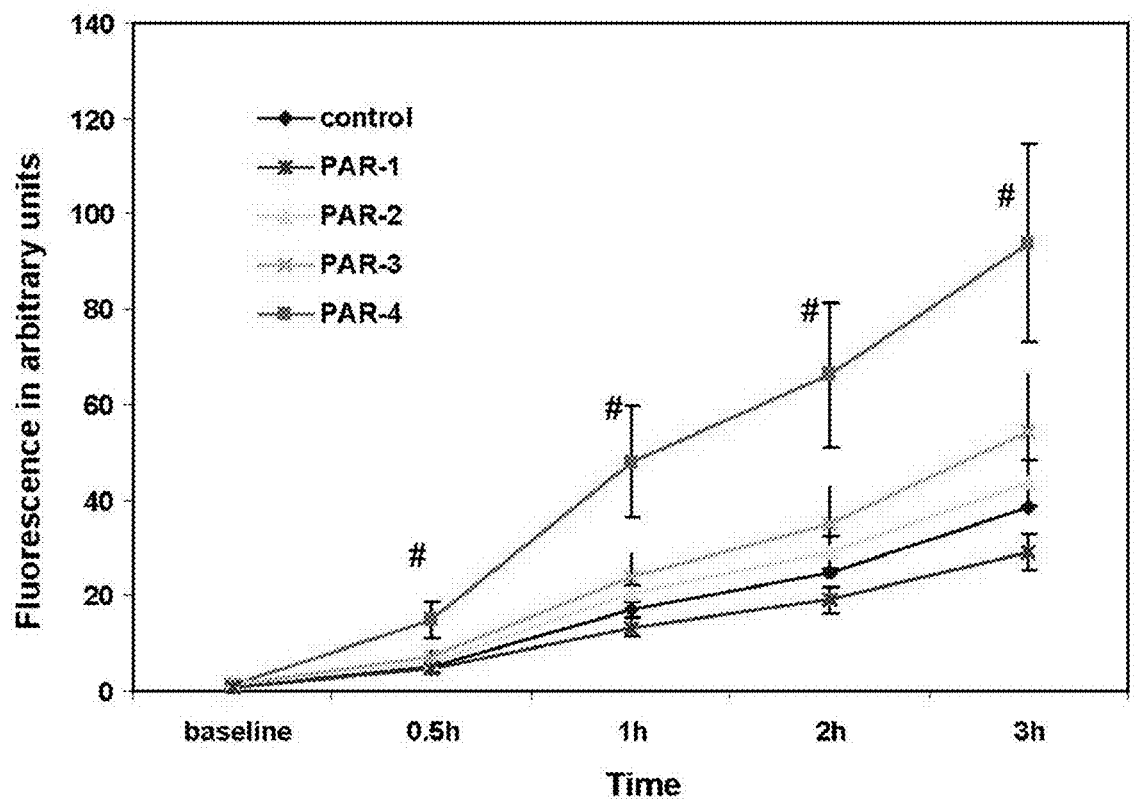
FIG. 5 provides time course of fluorescence emission of neutrophils incubated with DCFH-DA probe in the presence 100 mM soluble peptides which activate PAR-1, PAR2, PAR-3 or PAR-4. # P<0.01 compared to control. The data represents the mean±SD. This is a representative experiment of 3 experiments conducted in triplicate or quadruplicate.

PAR-4 activation was shown to result in the activation of neutrophil oxidative metabolism. Following the observed effect of α1 antichymotrypsin, a cathepsin G inhibitor, on neutrophil oxidative activity, the effect of specific soluble ligands of PARs on this activity was tested next. The data showed that activation of PAR-4 and not PAR-1, PAR-2 or PAR-3 (FIG. 5) resulted in a significantly accelerated rate of oxidation of the DCFH probe further supporting a role for a cathepsin G-PAR-4 mechanism in the observed spontaneous activation of neutrophil oxidative metabolism.

Figure 6A:
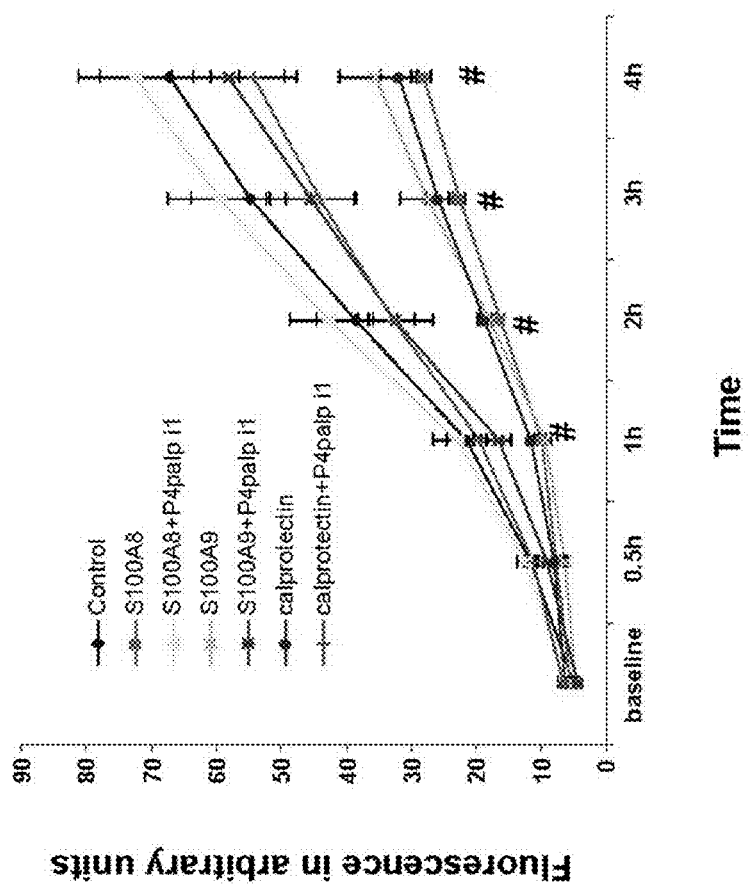
FIGS. 6A-6B show time course of fluorescence emission of neutrophils incubated with DCFH-DA probe in the presence 100 mM soluble peptide which activates PAR-4, 3 mM P4-pali1 (a specific inhibitor of PAR-4) (FIG. 6A) and S100A8, S100A9 and their combination at 10 mg/ml. # P<0.01 compared to control (FIG. 6B). The data represents the mean±SD. This is a representative experiment of 3 experiments conducted in triplicate or quadruplicate.
Figure 6B:
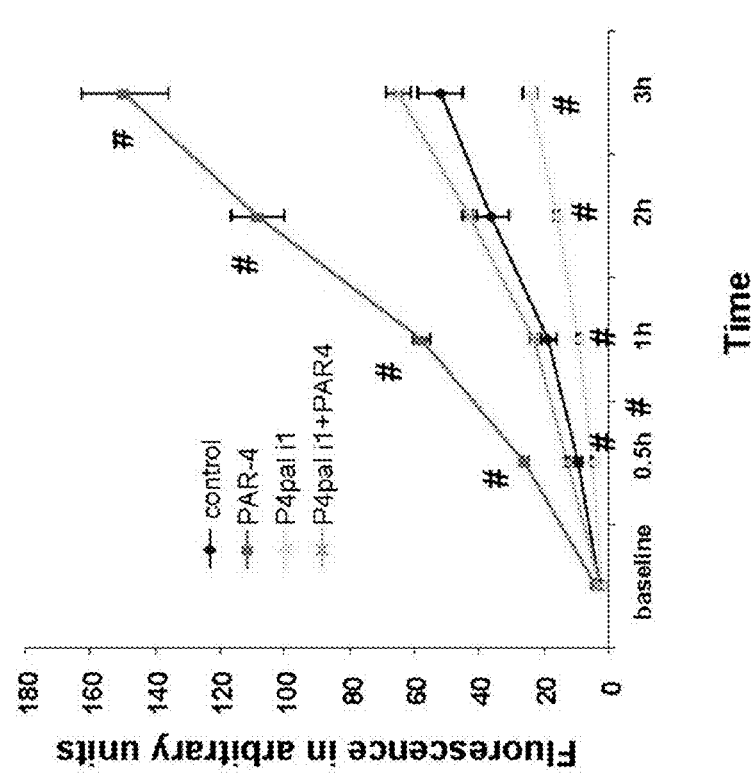

Pepducin targeting PAR-4 inhibits the effect of S100A8 on spontaneous neutrophil oxidative metabolism. In order to confirm the possible involvement of PAR-4 in the activity of S100A8/A9 and in the spontaneous oxidative metabolism of neutrophils[32], the ability of a palmitoylated peptide inhibitor of PAR-4 (pepducin P4pal-i1) [29, 32] to block S100A8/A9 activity was tested. In the presence of 2.5 μM P4pal-i1, spontaneous oxidative metabolic activity was reduced (FIG. 6A). The data showed that P4pal-i1 also blocked the ability of the PAR-4 activating peptide to enhance oxidative metabolism (FIG. 6A). Finally, P4pali1 blocked the ability of S100A8, S100A9 and calprotectin (S100A8/A9 in combination) to inhibit the spontaneous oxidative metabolic activity of neutrophils (FIG. 6B).

Figure 7A:
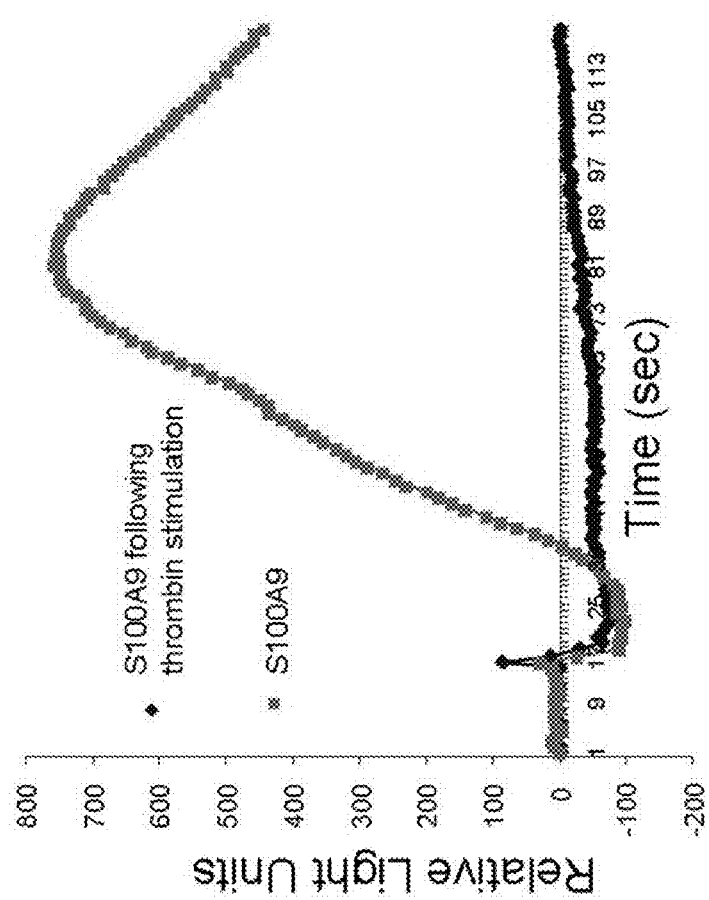
FIGS. 7A-7B illustrate calcium flux response to 10 mg/ml S100A8 (FIG. 7A) or S100A9 (FIG. 7B) in Chem-3 cells with or without previous stimulation with 10 nM thrombin.
Figure 7B:
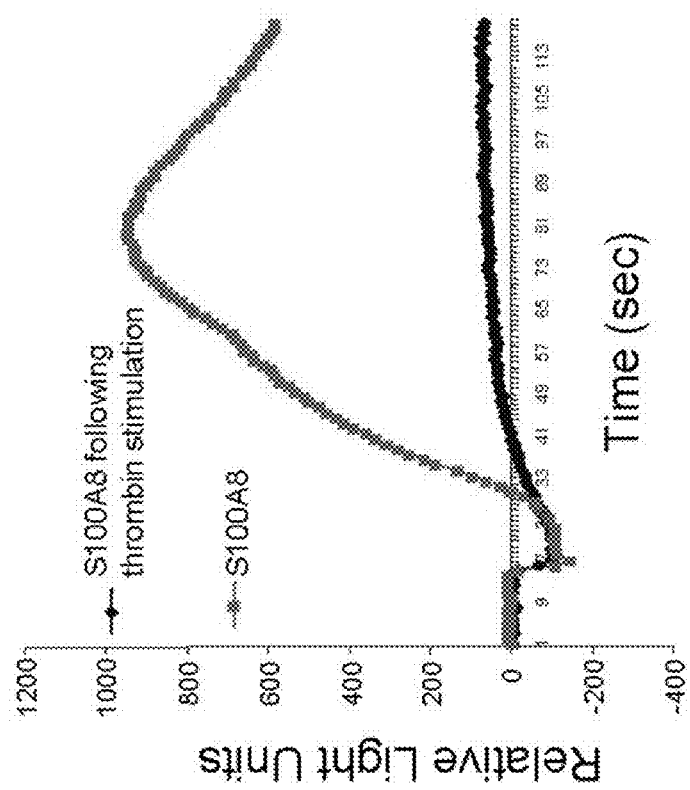

Thrombin-S100A8/A9 cross-desensitization was studied. The experiments with the PAR-4 specific inhibitor (pepducin P4pali-1) pointed to the involvement of PAR-4 in the measured S100 activity. I sought next to determine, whether S100A8 and S100A9 had a direct activity on PAR-4. The next set of experiments was conducted by testing the ability of thrombin (an activator of PAR-4) and S100A8/A9 to cross desensitize PAR-4 based on [33]. S100A8 and S100A9 and thrombin individually trigger calcium flux in Chem-3 cells in a dose dependent manner. The ability of thrombin to desensitize Chem3 cells to S100A8 or S100A9 stimulation was tested next. The data showed that stimulation with 10 nM thrombin resulted in a desensitization of Chem-3 cells to further stimulation with either 10 μM S100A8 (FIG. 7A) or 10 μM S100A9 (FIG. 7B).

Figure 8A:
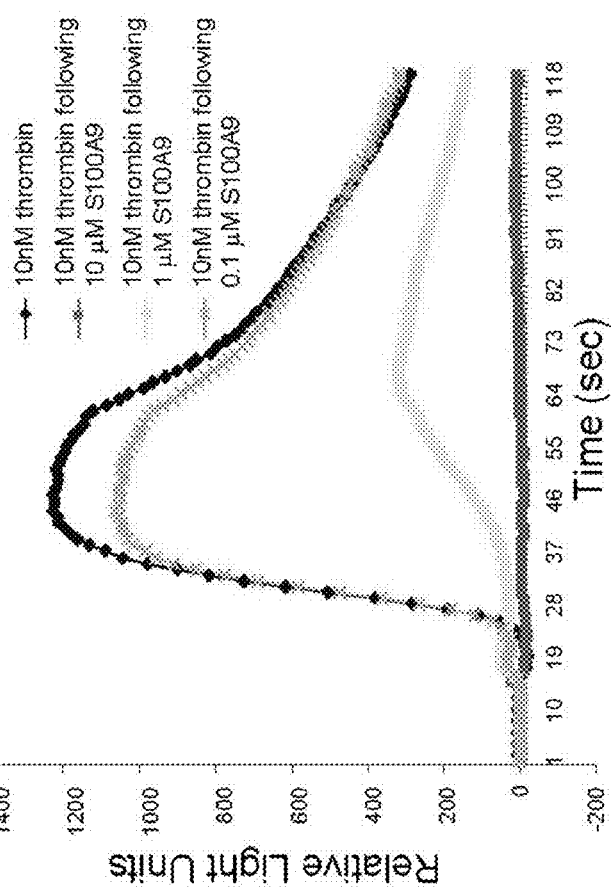
FIGS. 8A-8B display calcium flux response to nM thrombin in PAR-4 expressing cells previously stimulated with different concentrations of S100A8 (FIG. 8A) or S100A9 (FIG. 8B).
Figure 8B:
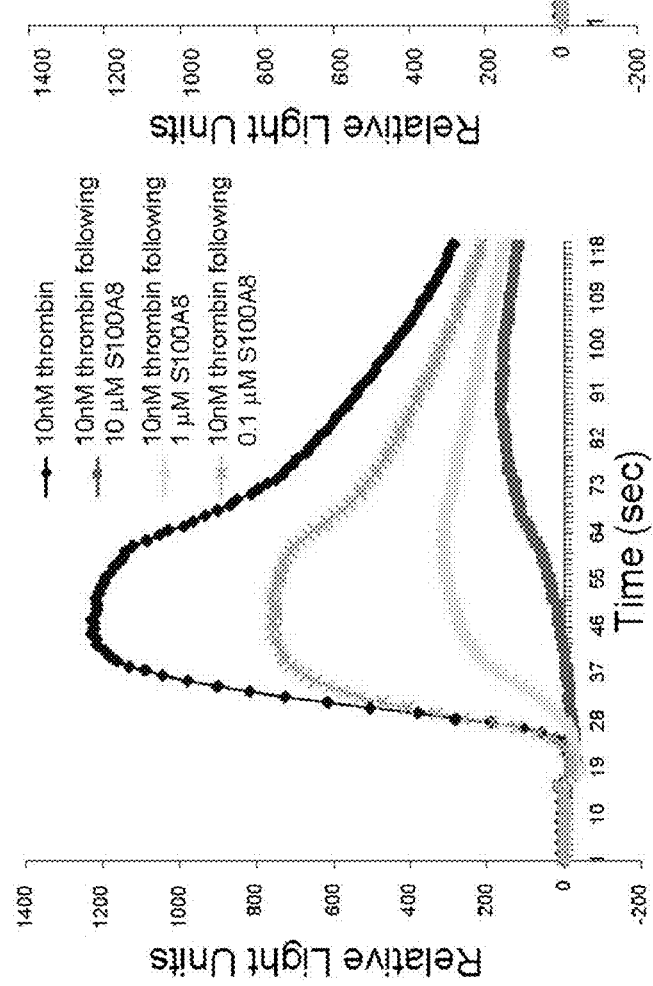

The ability of S100A8 and S100A9 to activate calcium flux in PAR-4 expressing cells was tested. Both S100A8 and S100A9 activated calcium flux in those cells (data not shown). Stimulation of calcium flux with 10 nM thrombin in PAR-4 expressing cells were tested following previous treatment with different concentrations of S100A8 or S100A9. The data showed that treatment with either S100A8 (FIG. 8A) and S100A9 (FIG. 8B) dose dependently desensitized PAR-4 expressing cells to thrombin activation.

S100A8 and S100A9 were shown to inhibit the stimulated activation of neutrophils oxidative metabolism. In the further experimentation the effects of S100A8 and S100A9 on PMA stimulation of neutrophil oxidative metabolism were examined. The data indicated that S100A8 and S100A9 produced a dose dependent inhibition of PMA activation of neutrophils (FIG. 3B-C), similar to what was observed above with the inhibition of the spontaneous oxidative activation.

The effect of S100A8 and S100A9 together and each alone was further tested on the rate at which LPS stimulated neutrophil. The data indicated that at concentrations ranging from 2.5 to 10 μg/ml of protein S100A8 and S100A9 strongly inhibited LPS stimulation of neutrophil oxidative activity (FIG. 4 A-C) further indicating that S100A8 and S100A9 anti-oxidative effect was not restricted to the spontaneous activation of neutrophil but was also relevant to controlled stimulated oxidative activation.

S100A8/A9 anti-oxidative effect is mediated by adenosine metabolites.

To test whether S100A8/A9 activity was mediated through adenosine metabolites, I next examined their effect on PMN oxidative metabolism in the presence of adenosine deaminase (ADA1), an enzyme which deaminates adenosine to inosine and inhibit its anti-oxidative functions in humans [51]. The data indicated that whereas S100A8 and S100A9 inhibited both the spontaneous and LPS stimulated oxidative metabolism at concentration ranging from 10 to 2.5 μg/ml (FIG. 9A-9B), this effect was partially or fully abrogated in the presence of ADA1 (FIG. 9C-9D). PMNs express several purinergic receptors including A2A and A3 receptors [49]. Those two receptors have been implicated in the inhibition leukocytes oxidative metabolism [47, 48, 52]. Accordingly, the inhibition of A2A and A3 adenosine receptors on S100A8/A9 anti-oxidative effect was tested next. The data indicated that inhibitors of A3 receptors abrogated the anti-oxidative effects of S100A8 and S100A9 (FIG. 10 A-10B) on LPS stimulated and on the constitutive oxidative metabolism of neutrophils. Inhibitors of A2A had a more modest effect whereas inhibitors of A1 and A2B P1 adenosine or P2 purinergic receptors had no measurable effect.

One of the most important functions of neutrophils is the production of oxidative metabolites in order to kill invading microorganisms. The same oxidative metabolites may cause serious injury to host tissues and therefore their production must be tightly regulated. It was previously shown that calprotectin regulates neutrophil recruitment and thus plays a role in minimizing damage during inflammation. Here it is demonstrated that the calprotectin peptides S100A8 and S100A9 also inhibit spontaneous production of oxidative metabolites and thus reduce damage to host tissue when under conditions of mild stimulation.

The data presented above indicates as a whole that S100A8 and S100A9 inhibit the spontaneous activation of neutrophil oxidative metabolism through a pathway implicating PAR-4. Firstly the data showed that the addition of extrinsic S100A8 or S100A9 resulted in a marked, dose dependent reduction in the rate of DCFH oxidation. This inhibitory effect was abrogated if the S100 proteins were first boiled supporting a specific direct activity rather than a non-specific anti-oxidative effect.

Supporting the anti-oxidative effect of S100A8 and S100A9, I showed that blocking the intrinsic S100A8 or S100A9 with specific monoclonal antibodies resulted in acceleration in the rate of DCFH oxidation, an effect opposite to what was observed with the addition of extrinsic S100 proteins.

While the oxidative activity of neutrophils is referred to as spontaneous, it is important to note that this activity is likely the result of cell manipulation and derive from the experimental procedures. Nevertheless, the data showed that spontaneous oxidative metabolism of neutrophils had the hallmarks of a genuine controlled activation of neutrophil oxidative burst. The spontaneous activation was dependent on PKC activity [25] and on the specific action of the serine protease Cathepsin G [34], as demonstrated by the respective anti-oxidative effect of GFX and α1 antichymotrypsin. Consequently, while it may be difficult to interpret the biological relevancy of the so-called spontaneous activation of neutrophils, it presents the signaling hallmarks of a genuine neutrophil oxidative activation suitable for mechanistic signaling studies. Furthermore, the laboratory has explored stimulation with lipopolysaccharide (LPS) of neutrophil oxidative metabolism. The data indicates that LPS stimulation of neutrophil oxidative burst responds similarly as the spontaneous activation to S100A8, S100A9 and PAR4 activators/inhibitors.

Finally, the data implicated PAR-4 in the regulation of neutrophil oxidative activation by S100 proteins in three additional distinct manners. First, the data established that activation of PAR-4 and not PAR-1, 2 or 3 with a receptor-specific soluble ligand resulted in the acceleration of DCFH oxidation by neutrophils. Secondly, P4pal-i1, a specific inhibitor of PAR-4 [29], inhibited the spontaneous and the PAR-4 soluble ligand activation of neutrophil oxidative metabolism. Direct implication of PAR-4 in S100A8 and S100A9 activity was afforded by data demonstrating that P4pal-i1 blocked S100A8, S100A9 and calprotectin inhibitory activity on neutrophil oxidative metabolism. Thirdly, pre-treatment with thrombin desensitized chem 3 cells to S100A8 and S100A9 triggered calcium flux whereas S100A8 and S100A9 caused a dose dependent desensitization to thrombin of PAR-4 expressing cells.

The significant effect of proteolytic activity in the regulation of neutrophils oxidative functions (specifically that cathepsin G) has long been documented [34]. The concentrations at which S100 proteins were found to be active are within the range of biological relevant concentrations of calprotectin [35-37]. This would indicate that the antioxidative and potentially anti-inflammatory effect of S100A8/A9 may represent a threshold to overcome in the induction of acute inflammation. This model is supported by previous work in which data indicating that S100A8 and S100A9 repel neutrophils and inhibit their chemotaxis toward pro-inflammatory molecules [10, 28] was presented. In this previous work, it was also reported on the inhibitory effect of oxidation on S100A8 and S100A9 anti-chemotactic effect. The complex regulatory interaction between neutrophil oxidative metabolism and S100A8/A9 may therefore represent one more layer of complexity. S100A8/A9 may in fact regulate their own oxidation by modifying neutrophil oxidative metabolism.

It is important to note that while these assays were conducted with granulocytes purified on HISTOPAQUE (trademark of Sigma Chemical Company, St. Louis, Mo.) gradients, cell contamination is relevant especially in light of the difficulties in demonstrating expression of PAR-4 in peripheral neutrophils [38, 39] (an observation confirmed in the laboratory). It is likely that S100A8, S100A9, the PAR-4 agonist and antagonist influenced oxidative metabolism of neutrophils not directly but via other cell types such as platelets, a common granulocyte layer contaminant [40]. It is also worth mentioning that the target cell (s) of the anti-inflammatory effect of PAR-4 blockage remains elusive in-vivo [41].

While these data support the involvement of PAR-4 in S100A8 and S100A9 activity, others have reported that fragments of S100A9 activate a different member of the PAR family: PAR-2 [42]. This suggests that S100A8 and S100A9 may be promiscuous regulators of PARs rather than a specific regulator of PAR-4. The complexity of the PARs system lies also on the reported ability of PARs to heterodimerize with members of other class of receptors such as Toll-like receptor (TLR). For example, PAR-2 was shown to heterodimerize with TLR-4 [43], intriguingly others have reported the activation of TLR4 by S100A8 and S100A9 [44].

Finally the significance of PAR-4 in the regulation of inflammation [18, 19, 45] and its involvement in the protection against oxidative damage [46] indicate that S100A8 and S100A9 are potentially important regulators of inflammation-induced oxidative damage.

One of the most important functions of neutrophils is the production of oxidative metabolites in order to kill invading microorganisms. The same oxidative metabolites may cause serious injury to host tissues. Their production must therefore be tightly regulated. The data included in this report indicate that S100A8 and S100A9 inhibit the spontaneous and stimulated oxidative metabolism of neutrophils in-vitro.

In further support for the anti-oxidative effect of S100A8 and S100A9, the data indicated that blocking the intrinsic S100A8 or S100A9 with specific monoclonal antibodies resulted in an acceleration of the rate of DCFH-DA oxidation, an effect opposite to what was observed with the addition of extrinsic S100 proteins. This finding supports the belief that S100A8/A9 plays a biologically relevant anti-oxidative function in regulation of neutrophil activation.

While the present inventor refers to the oxidative activity of neutrophils as spontaneous, this activity is believed the result of cell manipulation and may derive, at least in part, from the experimental procedures. Nevertheless, the data showed that spontaneous oxidative metabolism of neutrophils had the hallmarks of a genuine controlled activation of neutrophil oxidative burst. The spontaneous activation was dependent on PKC activity [25] as demonstrated by the effect of GFX. Consequently, whereas it may be difficult to interpret the biological relevancy of the so-called spontaneous activation of neutrophils, it presents the signaling hallmarks of a genuine neutrophil oxidative activation suitable for mechanistic signaling studies.

Beyond the spontaneous activation, the data clearly indicated that S100A8 and S100A9 inhibited the PMA and the biologically relevant LPS stimulation of neutrophil oxidative metabolism. It is believed that increased plasma, salivary or fecal levels of S100A8/A9 observed in association with inflammation [53-55] are aimed in part at diminishing the oxidative activation of neutrophils and protect the organism against exaggerated immune response concentrations recorded during acute inflammation [56-58] and in a syndrome of hypercalprotectinaemia [7] associated with opportunistic infections and auto-immune conditions. It is therefore believed that S100A8/A9 may reach biologically relevant anti-oxidative concentration in-vivo.

Whereas the exact mechanism(s) by which S100A8 and S100A9 exert their anti-oxidative effect remains elusive, the data indicated that adenosine metabolites were implicated.

Deamination of adenosine resulted in a loss of S100A8/A9 activity. Moreover, pharmaceutical agents targeting adenosine receptors also partially or fully reversed the anti-oxidative effect of the S100A8 and S100A9. The contribution of adenosine metabolites in the regulation of neutrophils or monocytes oxidative metabolism as well as their association with redox-dysregulation associated conditions has been widely reported [47, 48, 59]. Targeting adenosine signaling to reduce oxidation related damage has also been successfully pursued [56-58] The implication of adenosine metabolites in S100A8/A9 produced anti-oxidative effect is however novel and potentially valuable in the pursuit of adenosine related therapeutic interventions in conditions associated with deleterious inflammation and redox imbalance.

The concentrations at which S100A8 and S100A9 inhibited neutrophil oxidative metabolism so as to reduce the damage in a human or animal suffering from tachycardia, bradycardia, hypotension, atherosclerosis, embolism, thromboembolism, induced g-forces, septic shock, ischemia, hypoxia, an infarct event (such as cardiac infarction) and/or physical and/or psychological stresses, are within the range of 0.01 to 10 μg/ml in the bloodstream, to be administered by a parenteral route, for example, by intravenous injection. Exemplary dosages for an adult human are in the range of from about 0.05 to 10, 0.25 to 10, or 0.5 to 3 mg/kg body weight. Advantageously, the S100A8 and/or S100A9 is administered within 0.5 minutes up to 24 hours, or 0.5 minutes up to 4 or 6 hours, prior to an anticipated event or stress, especially one associated with hypoxia, or within about 0.5 minutes or less up to 24 hours, 0.5 minutes up to 4 or 6 hours, after an event associated with one of the foregoing events associated with deleterious effects including but not limited to one set forth above, for example, an event associated tissue damage due to oxidative stressors.

The results provided herein designate S100A8 and S100A9 proteins as targets for attenuation of the damage caused by "disregulated" acute inflammation, hypoxic conditions, reperfusion or potential reperfusion oxidative damage, ischemia-associated damage, infarct-associated damage and/or oxidative damage associated with physical and/or psychological stress.

Amelioration of wound closure rates in psychologically stressed animals treated with ala$^{42}$S100A8 was studied. Photoplanometric analysis of wound size indicated that, across the days since wounding, there was a significant effect on wound closure for both the "stress (RST)/no stress (FWD)" and "treatment group". For the "stress/no stress" condition, restraint animals experienced a delay in wound closure when compared to control animals ($F=6.971$, $p=0.001$). As soon as day 1 post-wounding, average wound size (in percentage of their original size) were significantly larger in restraint stressed animals (RST) when compared to control animals (FWD). Additionally, the three treatment groups; no treatment (saline control), ala$^{42}$S100A8 and WTS100A8 had statistically significant wound closure rates across time across time ($F=10.29$, $p=0.000$) with the control group exhibiting the most closure followed by ala$^{42}$S100A8 treated wounds (FIG. 11A). From day 2 on, average wound size in stressed animals treated with ala$^{42}$S100A8 was significantly smaller than the average wound size in stressed animals treated with saline ($t_{18}$ ranging 3.162 to 6.080 with all $p=0.000$ except day 2 where $p=0.01$). Wound closure in stressed animals treated with ala$^{42}$S100A8 displayed a closure rate similar to the closure rates observed in the non stressed food and water deprived (FWD) group.

A similar treatment of the wounds, immediately after wounding with wild type S100A8 (WTS100A8) resulted in a partial acceleration in wound closure rate in stressed animals. This effect did not reach statistical significance when compared to the closure rate in the stressed animals treated with saline (FIG. 11A). In additional experiments, daily administration of ala$^{42}$S100A8 to the wounds was tested for its ability to accelerate wound closure (FIG. 11B). Mice treated with repeated daily injection of saline (FWD multiple) displayed wound closure rates similar to that of single saline treatment mice (FWD saline). Daily injections of ala$^{42}$S100A8 did not result in the amelioration of wound closure rates observed with a single application post-wounding. Instead, daily treatment with ala$^{42}$S100A8 resulted in a significant delay in wound closure starting at day 4 post-wounding in non-stressed animals (FWD multiple v. FWD ALA42 ($t_{18}$=−2.799, $p=0.012$; $t_{18}$=−3.152, $p=0.006$ for day 4 and day 5 respectively).

The effect of ala$^{42}$S100A8 on wound bacterial clearance was studied in the mouse stress model system. To assess the effect of anti-inflammatory ala$^{42}$S100A8 on bacterial clearance, the effect of a single local administration of ala$^{42}$S100A8 on wound bacterial counts was tested next. Our previous work demonstrated that, ala$^{42}$S100A8 inhibited neutrophil recruitment in-vivo (Sroussi et al., 2006). The possibility that ala$^{42}$S100A8 treatment, applied immediately post-wounding, would cause a decrease in bacterial clearance secondary to its anti-inflammatory effect was tested. Accordingly bacterial counts in the wound of ala$^{42}$S100A8 and vehicle (saline) treated were measured at day-1 and day-5 post wounding in stressed and control mice. Firstly, the data indicated that restraint stress in this model resulted in a dramatic increase in wound bacterial counts both at day 1 (FIG. 12) and day 5 (FIG. 12B) post-wounding. This finding was in accordance with data published by others (Rojas et al., 2002). Secondly, ala$^{42}$S100A8 treatment resulted in a statistically significant increase in wound bacterial counts in FWD mice on day 1 post wounding ($t_{16}$=−6.179, $p=0.000$) (FIG. 12 A). By day 5 post wounding, bacterial counts had reverted to control values in ala$^{42}$S100A8-treated FWD mice (FIG. 12B). In contrast, statistically significant reduction in bacterial loads were recorded on both day 1 and 5 ($t_{18}$=2.896, $p=0.01$ and $t_{16}$=7.492, $p=0.000$ respectively) in the wounds of stressed mice treated with ala$^{42}$S100A8 when compared to saline treated wounds in stressed mice (FIG. 12 B).

The data collected indicate that in the SKH-1 mouse model psychological stress caused a delay in dermal wound closure associated with defective bacterial clearance. The delay in wound closure was observed as early as one day after wounding and the defective bacterial clearance was measured throughout the stress cycles at day 1 and day 5 post wounding. Those observations are in accordance with data reported in previous studies (Padgett et al., 1998; Rojas et al., 2002).

The data also indicated that a single local application of ala$^{42}$S100A8 post-wounding ameliorated the rate of wound closure in wounds impaired by restraint stress. In effect, the rate of wound closure in stressed mice is restored to control levels with ala$^{42}$S100A8 treatment of the wound. A similar application of wild type S100A8 (WTS100A8) partially ameliorated delayed wound closure caused by stress but to a much lesser extent than ala$^{42}$S100A8. Ala$^{42}$S100A8 is a molecule engineered to inhibit neutrophil recruitment in-vivo in an oxidative condition, which would inhibit the function of WTS100A8 (Sroussi et al., 2006). Since stress impaired wound closure was shown to be reversed by hyperbaric oxygen therapy (HBOT) (Gajendrareddy et al., 2005) in the SKH-1 model, the greater effect of ala$^{42}$S100A8 over WTS100A8 on wound closure rates offers further support to redox homeostasis as a mechanism for the dysregulation of wound closure in psychologically stressed animals. Alternatively, while not directly involved in the mechanism of wound healing impairment, redox signaling and its manipulation may represent practical therapeutic targets to ameliorate impaired wound healing.

Treatment with ala$^{42}$S100A8 caused a significant increase in wound bacterial counts at day 1 in control animals. This increase in bacterial count is unlikely to be clinically significant as supported by normal wound closure rates in non-stressed control animals treated with ala$^{42}$S100A8 and by restoration of normal bacterial count by day 5 post-wounding. Conversely, in restraint stressed animals, ala$^{42}$S100A8 caused a decrease in bacterial counts. Whether this decrease in bacterial counts explains the beneficial effect of ala$^{42}$S100A8 on wound closure rates is unknown. The data on bacterial clearance in stressed animals treated with ala$^{42}$S100A8 indicated a modest reduction in bacterial counts which remain well above the bacterial counts observed in control food and water deprived control mice. This denoted that ala$^{42}$S100A8 restored normal wound closure rates in stressed animals without restoring normal bacterial wound clearance. Similar observations were made with glucocorticoid receptor antagonists in the same SKH-1 ameliorates wound healing rates in stressed SKH-1 mice (Padgett et al., 1998) without reestablishing normal wound bacterial clearance (Rojas et al., 2002). The magnitude of the observed improvement in bacterial clearance in stressed mice treated with ala$^{42}$S100A8 was similar to what was observed with RU486, a glucocorticoid antagonist (Rojas et al., 2002). Altogether, it appears that while restraint stress in this model is causative for delay of wound closure and defective bacterial clearance, no clear and simple causality can be established between a defective bacterial clearance and a delay in wound closure rates in this model. The lack of a simple causality between those two outcomes is further supported by observations that bacterial inoculation of wounds in this model can accelerate wound closure rates (Rojas et al., 2002). It is therefore unlikely that ala$^{42}$S100A8 affected wound closure rates by altering bacterial clearance. The aim of the bacterial studies in this work was to ascertain that ala$^{42}$S100A8, an anti-inflammatory molecule, would not impair bacterial clearance to the point where it would represent a clinical significant factor. The data support this.

Finally, daily injection of ala$^{42}$S100A8 did not ameliorate wound closure rates and may have caused a significant late delay in wound closure in control non-stressed animals. This would imply that the effects of ala$^{42}$S100A8 while beneficial initially, may compromise healing at later stages of healing possibly at the proliferative stage. It is possible that applications of ala$^{42}$S100A8 in later phases of wound healing, may also interfere with the beneficial recruitment of macrophage (Savill et al., 1989) or alternatively that ala$^{42}$S100A8 may exert additional activities with detrimental consequences on the rate of wound closure such as an anti proliferative effect (Yui et al., 2003). The timing of a S100A8 based anti-inflammatory intervention in improving wound healing is therefore critical in establishing its overall effect on wound healing. Understanding the mechanisms of action of ala$^{42}$S100A8 and its temporal relationship with the well-orchestrated wound healing process may help the laboratory design S100A8-based mechanistically and temporally targeted strategy for the treatment of impaired wound healing.

All references cited herein are hereby incorporated by reference to the extent they are not inconsistent with the present disclosure. These references also reflect the level of skill in the art(s) relevant to the understanding and practice of the present invention.

Although the description herein contains certain specific information and examples, these should not be construed as limiting the scope of the invention but as merely providing illustrations of some of the presently preferred embodiments of the invention. For example, thus the scope of the invention should be determined by the appended claims and their equivalents, rather than by the examples given.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, starting materials, synthetic methods, and other than those specifically exemplified can be employed in the practice of the invention without resort to undue experimentation. All art-known functional equivalents, of any such methods, device elements, starting materials, are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The following definitions are provided to clarify their specific use in the context of the invention.

The exact formulation, route of administration and dosage can be chosen by the individual physician in view of the patient's condition (see e.g. Fingl et. al., in The Pharmacological Basis of Therapeutics, 1975, Ch. 1 p. 1).

It should be noted that the attending physician would know how to and when to terminate, interrupt, or adjust administration due to toxicity, or to organ dysfunctions, in a patient (human or animal) receing the pharmaceutical composition comprising S100A8 and/or S100A9. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine, and it is understood that it is advantageous to use S100A8 and/or S100A9 proteins in therapeutic compositions which are ultimately derived from the same species as the patient, although modifications such as those described herein can be made to those proteins.

Depending on the specific conditions being treated and the targeting method selected, such agents may be formulated and administered systemically. Techniques for formulation and administration may be found in Alfonso and Gennaro (1995). Suitable routes may include, for example, intravenous, oral, rectal, transdermal, vaginal, transmucosal, or intestinal administration; parenteral delivery including intramuscular, subcutaneous, or intramedullary injections, as well as intrathecal, intravenous, or intraperitoneal injections, with the understanding that the S100A8 and/or S100A9 exert their beneficial effects systemically rather than in a localized fashion.

For injection, the agents of the invention may be formulated in sterile aqueous solutions, such as in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically.

The pharmaceutical compositions of the present invention may be manufactured in a manner that is itself known, e.g., by means of conventional mixing, dissolving, granulating, levitating, emulsifying, encapsulating, entrapping or lyophilizing processes.

Pharmaceutical formulations for parenteral administration include aqueous solutions of the active compounds in water-soluble form. Optionally, the suspension may also contain suitable stabilizers or agents which increase the solubility of the compounds to allow for the preparation of highly concentrated solutions.

One skilled in the art would readily appreciate that the present invention is well adapted to carry out the objects and obtain the ends and advantages mentioned, as well as those inherent therein. The methods described herein as presently representative of embodiments are exemplary and are not intended as limitations on the scope of the invention. Changes therein and other uses will occur to those skilled in the art, which are encompassed within the spirit of the invention, are defined by the scope of the claims.

Materials and Methods

Expression and Purification of Recombinant S100 Proteins

Recombinant S100A8 and S100A9 protein were produced and purified based on standard methods as previously described [10, 28]. Briefly, both proteins were cloned in a pGEX-2T GST vector (Amersham, Piscataway, N.J.). The proteins were expressed in *Escherichia coli* as GST fusion proteins. The GST tag was cleaved during the purification process. Protein concentration was assessed through a Bradford protein assay (Pierce, Rockford, Ill.).

Reagents

Dichlorofluorescein diacetate (DCFH-DA) and Bisindolylmaleimide I (GFX 109203X) (GFX for short) were purchased from EMD Calbiochem (San Diego, Calif.). PAR-1 (TFLLRN), PAR2 (SLIGKV-NH2), PAR3 (TFRGAP-NH2), and PAR4 (GYPGQV-NH2) soluble peptide agonists and elafin were purchased from Anaspec (San Jose, Calif.). α1-Antichymotrypsin from human plasma, phorbol 12-myristate 13-acetate (PMA), lipopolysaccharides (LPS) from *Escherichia coli*, N-(2-methoxyphenyl)-N'-[2-(3-pyridinyl)-4-quinazolinyl]-urea (VUF5574) (an A3 adenosine antagonist) and Human adenosine deaminase (ADA1), from human erythrocytes were purchased from Sigma-Aldrich (St. Louis, Mo.). A palmitoylated peptide, p4pal-i1 (C15H31CONH-ATGAPRLPST), which specifically blocks PAR-4 [29] was synthesized and purified >89% by peptide 2 (Chantilly, Va.). Mouse monoclonal antibody directed against S100A8 or S100A9 were purchased from Novus Biologicals (Littleton, Colo.).

Isolation of Peripheral Neutrophils

Human peripheral neutrophils were isolated from heparinized blood donated by healthy volunteers according to a protocol approved by the University of Illinois Institutional Review Board. The cells were isolated using a Histopaque™ gradient (Sigma) according to the manufacturer's instructions. Cell viability and identity was confirmed by trypan blue staining. Live cells and neutrophils represented at least 95% of isolated leukocytes.

Assay for Oxidative Activation of Neutrophils

The method for the measurement of oxidative activation of neutrophils was based on the ROS-dependent oxidation of DCFH-DA to DCF and was adapted from Ciapetti et al [21]. DCFH-DA crosses the cell membrane and is hydrolyzed by nonspecific esterases to nonfluorescent DCFH. Its oxidation by ROS results in the generation of highly fluorescent DCF [30]. DCFH-DA is therefore a widely accepted probe for the measurement of an overall index of oxidative activity. DCFH-DA was purchased from Calbiochem (Madison, Wis.). The assays were run in clear bottom black 96-well plate. "Edge effects" (a higher fluorescence in edge wells) were avoided by using only center wells. Briefly, 50 µl of Dulbecco's Phosphate Buffered Saline (DPBS) containing DCFH-DA was added to each well with the final concentration of 10 mg/ml. S100 proteins or PKC inhibitors were diluted in the wells. Just before a baseline reading 100,000 neutrophils in 50 µl PBS were placed in each well. 96-well plates were incubated at 37° C. and 5% $CO_2$ and were read at baseline (immediately after cell addition to the plates) and at indicated time points in a Spectra Max Gemini XS fluorescent plate reader. The excitation wavelength was 485 and the reading was done at 530 nm. Wells with no DCFH-DA were used to measure background fluorescence which was subtracted from each reading. Controls with no cells were also analyzed and display no increased fluorescence over time. All assays were conducted in triplicate or quadruplicate wells.

Thrombin-S100A8/A9 Cross-Desensitization Assays

Screening for S100A8 and S100A9 activity on thrombin receptors including thrombin receptor desensitization were conducted with calcium flux assays in Chem 3 and PAR-4 expressing Chem.-1 cells by Millipore's GPCRProfiler(R) Service (Millipore, St. Charles, Mo.; see website Millipore website on the internet).

Data Analysis

In order to avoid differences between donors, experimental procedures and plate to plate variation, all experimental conditions and statistical analysis were run within one plate inclusive of all positive and negative controls. Single sample t-tests were calculated to test the S100A8, S100A9 and combined proteins in comparison to the control wells with alpha set to $\leq 0.05$ to determine statistical significance. Comparisons between the S100A8, S100A9 and combined proteins were calculated with two sample t-tests using SPSS (SPSS Inc., Chicago, Ill.) with alpha set to $\leq 0.05$ to determine statistical relevance.

In certain experiments, Repeated Measure ANOVAs were performed with the 'days since wounding' as the Within-Subjects factor and "stress/no stress" and "treatment group" as the Between-Subjects factors. Bonferroni post-hoc analyses were performed for all statistically significant main effects.

In measuring bacterial clearance, Two-Way ANOVAs were performed with 'colony count' as the dependent variable and "stress/no stress" and "treatment group" as the Between-Subjects factors Animal Wound Model for Stress This protocol was approved by the Committee on Animal Research at the University of Illinois at Chicago. Virus antibody-free, female SKH-1 mice, 5-6 weeks of age, were purchased from Charles River, Inc (Wilmington, Mass.). The animals were allowed to acclimate to the animal facility for at least one week prior to experimental procedures.

The restraint stress protocol is based on established procedures (Gajendrareddy et al., 2005; Mercado et al., 2002; Padgett et al., 1998). Restraint was initiated 3 days before wounding. Restraint stress (RST) in this model consists of confinement of mice within loosely fitting, well-ventilated 50 ml conical tubes for a period of 12-14 hours during their active nocturnal cycle. Animals were subjected to restraint for an additional five cycles on the day of wounding and for four days thereafter, then stress was discontinued. Mice do not feed during restraint; hence controls were deprived of food and water (FWD) during the restraint period.

For excisional wounds, mice were anesthetized with a single 0.25 ml intraperitoneal injection of Ketaset solution (Aveco, Fort Dodge, Iowa) at a concentration of 7.8 mg/ml, plus Rompum (Haver-Lockhart, Shawnee, Kans.) at 0.44 mg/ml. Each animal received two standardized circular cutaneous wounds with 3.5 mm punch (Miltex Instrument Company), placed just behind the shoulder blades with a biopsy punch.

For treatment of wounds, S100A8 and mutant ala$^{42}$S100A8 were produced, cleaved and purified from a GST fusion construct as previously described (Tugizov et al., 2005) (Sroussi et al., 2006). The endotoxin levels in the recombinant protein preparations were below 1 ng/µg of proteins as measured by the *Limulus* amoebocyte lysate assay (LAL) (Associates of Cape Cod, Falmouth, Mass.). Solutions of S100 proteins at a concentration of 1 µg/ml were used for those experiments. Introduction of S100A8 protein or control saline vehicle were conducted through local injection intradermally of 25 µl solution in the tissue surrounding the wounds with the help of Micro-Fine IV syringes 28G1/2 (Becton Dickinson, Franklin Lakes, N.J.). Careful wound manipulation ensured no direct disruption of the wound site. An additional 10 µl solution was applied directly to the wounds.

Wound biopsies were performed to evaluate bacterial clearance. Mice were anesthetized as described above. The dorsal area was cleaned with Betadine and a uniform, full-thickness wound located on the dorsum just below the shoulder blades was created with a sterile 6.0-mm punch (Miltex Instrument Company).

Wound infection was assessed with measurement of bacterial load at the wound site by methods adapted from Rojas (Rojas et al., 2002). At day 1 and day 5 post-wounding, mice were euthanized; wounds were collected with a 6-mm punch (see above) and homogenized in 1 ml of sterile PBS. Homogenates were serially diluted (1:10); plated in duplicate on BHI agar, and incubated for 15 h. Bacterial colonies were counted.

Measurement of Wound Sizes was done as follows. Beginning on the day of wounding (day 0), each animal's wounds were photographed daily until day 5 post-wounding. Photographs of the wound were obtained with a standard-sized dot placed next to the site. Digitized photographs were analyzed using photoplanimetry (Marucha et al., 1998). An investigator blinded to treatment group and day of photograph measured wound size. Wound size was expressed as the percentage of the wound area determined on every post-wounding day, compared with the original wound area.

A restraint stress model of impaired cutaneous wound healing is used to demonstrate the benefits of S100A8 and/or S100A9. SKH-1 female mice at 6-8 weeks of age are acclimated to their laboratory surrounds for 7-10 days. Then the mice are placed in well-ventilated 50 ml centrifuge tubes for three nocturnal cycles of restraint prior to wounding and five subsequent cycles (12-14 hrs). Control mice are deprived of food and water during the same time period but are allowed to roam freely in their Outcomes measured in this animal model include wound closure, bacterial clearance, gene and protein expression and histological studies of cell proliferation, angiogenesis, among others.

BIBLIOGRAPHY

1. Eckert, J. W., Abramson, S. L., Starke, J., Brandt, M. L. (1995) The surgical implications of chronic granulomatous disease. Am J Surg 169, 320-3.
2. Gordillo, G. M., Sen, C. K. (2003) Revisiting the essential role of oxygen in wound healing. Am J Surg. 186, 259-63.
3. Cave, A. C., Brewer, A. C., Narayanapanicker, A., Ray, R., Grieve, D. J., Walker, S., Shah, A. M. (2006) NADPH oxidases in cardiovascular health and disease. Antioxid Redox Signal. 8, 691-728.
4. Edgeworth, J., Gorman, M., Bennett, R., Freemont, P., Hogg, N. (1991) Identification of p-8, 14 as a highly abundant heterodimeric calcium binding protein complex of myeloid cells. J Biol Chem. 266, 7706-13.
5. Saito, Y., Saito, K., Hirano, Y., Ikeya, K., Suzuki, H., Shishikura, K., Manno, S., Takakuwa, Y., Nakagawa, K., Iwasa, A., Fujikawa, S., Moriya, M., Mizoguchi, N., Golden, B. E., Osawa, M. (2002) Hyperzincemia with systemic inflammation: a heritable disorder of calprotectin metabolism with rheumatic manifestations? J Pediatr. 140, 267-9.
6. Fessatou, S., Fagerhol, M. K., Roth, J., Stamoulakatou, A., Kitra, V., Hadarean, M., Paleologos, G., Chandrinou, H., Sampson, B., Papassotiriou, I. (2005) Severe anemia and neutropenia associated with hyperzincemia and hypercalprotectinemia. J Pediatr Hematol Oncol. 27, 477-80.
7. Sampson, B., Fagerhol, M. K., Sunderkotter, C., Golden, B. E., Richmond, P., Klein, N., Kovar, I. Z., Beattie, J. H., Wolska-Kusnierz, B., Saito, Y., Roth, J. (2002) Hyperzincaemia and hypercalprotectinaemia: a new disorder of zinc metabolism. Lancet 360, 1742-5.
8. Cornish, C. J., Devery, J. M., Poronnik, P., Lackmann, M., Cook, D. I., Geczy, C. L. (1996) S100 protein CP-10 stimulates myeloid cell chemotaxis without activation. J Cell Physiol 166, 427-37.
9. Ryckman, C., Vandal, K., Rouleau, P., Talbot, M., Tessier, P. A. (2003) Proinflammatory activities of S100: proteins S100A8, S100A9, and S100A8/A9 induce neutrophil chemotaxis and adhesion. J Immunol. 170, 3233-42.
10. Sroussi, H. Y., Berline, J., Palefsky, J. M. (2007) Oxidation of methionine 63 and 83 regulates the effect of S100A9 on the migration of neutrophils in vitro. J Leukoc Biol. 81, 818-24. Epub 2006 Nov. 30.
11. Pham, C. T. (2006) Neutrophil serine proteases: specific regulators of inflammation. Nat Rev Immunol. 6, 541-50.
12. Reeves, E. P., Lu, H., Jacobs, H. L., Messina, C. G., Bolsover, S., Gabella, G., Potma, E. O., Warley, A., Roes, J., Segal, A. W. (2002) Killing activity of neutrophils is mediated through activation of proteases by K+ flux. Nature. 416, 291-7.
13. Zarbock, A., Polanowska-Grabowska, R. K., Ley, K. (2007) Platelet-neutrophil-interactions: linking hemostasis and inflammation. Blood Rev. 21, 99-111. Epub 2006 Sep. 20.
14. Pham, C. T. (2008) Neutrophil serine proteases fine-tune the inflammatory response. Int J Biochem Cell Biol. 40, 1317-33. Epub 2007 Nov. 29.
15. Ossovskaya, V. S., Bunnett, N. W. (2004) Protease-activated receptors: contribution to physiology and disease. Physiol Rev. 84, 579-621.
16. Cumashi, A., Ansuini, H., Celli, N., De Blasi, A., O'Brien, P. J., Brass, L. F., Molino, M. (2001) Neutrophil proteases can inactivate human PAR3 and abolish the co-receptor function of PAR3 on murine platelets. Thromb Haemost. 85, 533-8.
17. Sambrano, G. R., Huang, W., Faruqi, T., Mahrus, S., Craik, C., Coughlin, S. R. (2000) Cathepsin G activates protease-activated receptor-4 in human platelets. J Biol Chem. 275, 6819-23.
18. Slofstra, S. H., Bijlsma, M. F., Groot, A. P., Reitsma, P. H., Lindhout, T., ten Cate, H., Spek, C. A. (2007) Protease-activated receptor-4 inhibition protects from multiorgan failure in a murine model of systemic inflammation. Blood. 110, 3176-82. Epub 2007 Jul. 19.
19. Houle, S., Papez, M. D., Ferazzini, M., Hollenberg, M. D., Vergnolle, N. (2005) Neutrophils and the kallikrein-kinin system in proteinase-activated receptor 4-mediated inflammation in rodents. Br J Pharmacol. 146, 670-8.
20. Koethe, S. M., Kuhnmuench, J. R., Becker, C. G. (2000) Neutrophil priming by cigarette smoke condensate and a tobacco anti-idiotypic antibody. Am J Pathol. 157, 1735-43.
21. Ciapetti, G., Granchi, D., Verri, E., Savarino, L., Cenni, E., Savioli, F., Pizzoferrato, A. (1998) Fluorescent microplate assay for respiratory burst of PMNs challenged in vitro with orthopedic metals. J Biomed Mater Res. 41, 455-60.
22. Farhadi, A., Keshavarzian, A., Fitzpatrick, L. R., Mutlu, E., Zhang, Y., Banan, A. (2002) Modulatory effects of plasma and colonic milieu of patients with ulcerative colitis on neutrophil reactive oxygen species production in presence of a novel antioxidant, rebamipide. Dig Dis Sci. 47, 1342-8.
23. Tan, A. S., Berridge, M. V. (2000) Superoxide produced by activated neutrophils efficiently reduces the tetrazolium salt, WST-1 to produce a soluble formazan: a simple colorimetric assay for measuring respiratory burst activation and for screening anti-inflammatory agents. J Immunol Methods. 238, 59-68.
24. Mohanty, J. G., Jaffe, J. S., Schulman, E. S., Raible, D. G. (1997) A highly sensitive fluorescent micro-assay of H2O2 release from activated human leukocytes using a dihydroxyphenoxazine derivative. J Immunol Methods. 202, 133-41.
25. Decoursey, T. E., Ligeti, E. (2005) Regulation and termination of NADPH oxidase activity. Cell Mol Life Sci. 62, 2173-93.
26. Guerreiro, J. B., Porto, M. A., Santos, S. B., Lacerda, L., Ho, J. L., Carvalho, E. M. (2005) Spontaneous neutrophil activation in HTLV-1 infected patients. Braz J Infect Dis. 9, 510-4. Epub 2006 Jan. 9.
27. Hsieh, S. C., Tsai, C. Y., Sun, K. H., Yu, H. S., Tsai, S. T., Wang, J. C., Tsai, Y. Y., Han, S. H., Yu, C. L. (1994) Decreased spontaneous and lipopolysaccharide stimulated production of interleukin 8 by polymorphonuclear neutrophils of patients with active systemic lupus erythematosus. Clin Exp Rheumatol. 12, 627-33.
28. Sroussi, F L Y., Berline, J., Dazin, P., Green, P., Palefsky, J. M. (2006) S100A8 Triggers Oxidation-sensitive Repulsion of Neutrophils. J Dent Res. 85, 829-33.
29. Leger, A. J., Jacques, S. L., Badar, J., Kaneider, N. C., Derian, C. K., Andrade-Gordon, P., Covic, L., Kuliopulos, A. (2006) Blocking the protease-activated receptor 1-4 heterodimer in platelet-mediated thrombosis. Circulation. 113, 1244-54. Epub 2006 Feb. 27.
30. LeBel, C. P., Ischiropoulos, H., Bondy, S. C. (1992) Evaluation of the probe 2',7'-dichlorofluorescin as an indicator of reactive oxygen species formation and oxidative stress. Chem Res Toxicol. 5, 227-31.
31. Ryckman, C., Gilbert, C., De Medicis, R., Lussier, A., Vandal, K., Tessier, P. A. (2004) Monosodium urate mono- 31. hydrate crystals induce the release of the proinflammatory protein S100A8/A9 from neutrophils. J Leukoc Biol.
32. Covic, L., Misra, M., Badar, J., Singh, C., Kuliopulos, A. (2002) Pepducin-based intervention of thrombin-receptor signaling and systemic platelet activation. Nat Med. 8, 1161-5. Epub 2002 Sep. 23.
33. Hoxie, J. A., Ahuja, M., Belmonte, E., Pizarro, S., Parton, R., Brass, L. F. (1993) Internalization and recycling of activated thrombin receptors. J Biol Chem. 268, 13756-63.
34. Kilpatrick, L., Johnson, J. L., Nickbarg, E. B., Wang, Z. M., Clifford, T. F., Banach, M., Cooperman, B. S., Douglas, S. D., Rubin, H. (1991) Inhibition of human neutrophil superoxide generation by alpha 1-antichymotrypsin. J Immunol. 146, 2388-93.
35. Muller, F., Froland, S. S., Aukrust, P., Fagerhol, M. K. (1994) Elevated serum calprotectin levels in HIV-infected patients: the calprotectin response during ZDV treatment is associated with clinical events. J Acquir Immune Defic Syndr. 7, 931-9.
36. Sweet, S. P., Denbury, A. N., Challacombe, S. J. (2001) Salivary calprotectin levels are raised in patients with oral candidiasis or Sjogren's syndrome but decreased by HIV infection. Oral Microbiol Immunol 16, 119-23.
37. Jung, D. Y., Park, J. B., Lee, E. N., Lee, H. A., Joh, J. W., Kwon, C. H., Ki, C. S., Lee, S. Y., Kim, S. J. (2008) Combined use of myeloid-related protein 8/14 and procalcitonin as diagnostic markers for acute allograft rejection in kidney transplantation recipients. Transpl Immunol. 18, 338-43. Epub 2007 Oct. 29.
38. Kannan, S. (2002) Role of protease-activated receptors in neutrophil degranulation. Med. Hypotheses. 59, 266-7.
39. Kahn, M. L., Nakanishi-Matsui, M., Shapiro, M. J., Ishihara, H., Coughlin, S. R. (1999) Protease-activated receptors 1 and 4 mediate activation of human platelets by thrombin. J Clin Invest. 103, 879-87.
40. Zahler, S., Kowalski, C., Brosig, A., Kupatt, C., Becker, B. F., Gerlach, E. (1997) The function of neutrophils isolated by a magnetic antibody cell separation technique is not altered in comparison to a density gradient centrifugation method. J Immunol Methods. 200, 173-9.
41. Weiler, H., Ruf, W. (2007) PAR4 antagonists in inflammation 10.1182/blood-2007-08-103812. Blood 110, 3091-3092.
42. Dale, C. S., Cenac, N., Britto, L. R., Juliano, M. A., Juliano, L., Vergnolle, N., Giorgi, R. (2006) The C-terminus of murine S100A9 protein inhibits hyperalgesia induced by the agonist peptide of protease-activated receptor 2 (PAR2). Br J Pharmacol. 149, 374-84. Epub 2006 Sep. 11.
43. Rallabhandi, P., Nhu, Q. M., Toshchakov, V. Y., Piao, W., Medvedev, A. E., Hollenberg, M. D., Fasano, A., Vogel, S. N. (2008) Analysis of proteinase-activated receptor 2 and TLR4 signal transduction: a novel paradigm for receptor cooperativity. J Biol Chem. 283, 24314-25. Epub 2008 Jul. 11.
44. Vogl, T., Tenbrock, K., Ludwig, S., Leukert, N., Ehrhardt, C., van Zoelen, M. A., Nacken, W., Foell, D., van der Poll, T., Sorg, C., Roth, J. (2007) Mrp8 and Mrp14 are endogenous activators of Toll-like receptor 4, promoting lethal endotoxin-induced shock. Nat Med. 13, 1042-9. Epub 2007 Sep. 2.
45. Asfaha, S., Cenac, N., Houle, S., Altier, C., Papez, M. D., Nguyen, C., Steinhoff, M., Chapman, K., Zamponi, G. W., Vergnolle, N. (2007) Protease-activated receptor-4: a novel mechanism of inflammatory pain modulation. Br J Pharmacol. 150, 176-85. Epub 2006 Dec. 18.
46. Strande, J. L., Hsu, A., Su, J., Fu, X., Gross, G. J., Baker, J. E. (2008) Inhibiting protease-activated receptor 4 limits myocardial ischemia/reperfusion injury in rat hearts by unmasking adenosine signaling. J Pharmacol Exp Ther. 324, 1045-54. Epub 2007 Nov. 30.
47. van der Hoeven, D.; Wan, T. C.; Auchampach, J. A. Activation of the A(3) adenosine receptor suppresses superoxide production and chemotaxis of mouse bone marrow neutrophils. Mol Pharmacol 74:685-696; 2008.
48. Sun, W. C.; Moore, J. N.; Hurley, D. J.; Vandenplas, M. L.; Linden, J.; Cao, Z.; Murray, T. F. Adenosine A2A receptor agonists inhibit lipopolysaccharide-induced production of tumor necrosis factor-alpha by equine monocytes. Vet Immunol Immunopathol 121:91-100; 2008.
49. Chen, Y.; Corriden, R.; Inoue, Y.; Yip, L.; Hashiguchi, N.; Zinkernagel, A.; Nizet, V.; Insel, P. A.; Junger, W. G. ATP release guides neutrophil chemotaxis via P2Y2 and A3 receptors. Science 314:1792-1795; 2006.
50. Aguiar-Passeti, T.; Postol, E.; Sorg, C.; Mariano, M. Epithelioid cells from foreign-body granuloma selectively express the calcium-binding protein MRP-14, a novel down-regulatory molecule of macrophage activation. J Leukoc Biol 62:852-858; 1997.
51. Levy, O.; Coughlin, M.; Cronstein, B. N.; Roy, R. M.; Desai, A.; Wessels, M. R. The adenosine system selectively inhibits TLR-mediated TNF-alpha production in the human newborn. J Immunol 177:1956-1966; 2006.
52. Broussas, M.; Cornillet-Lefebvre, P.; Potron, G.; Nguyen, P. Adenosine inhibits tissue factor expression by LPS-stimulated human monocytes: involvement of the A3 adenosine receptor. Thromb Haemost 88:123-130; 2002.
53. Golden, B. E.; Clohessy, P. A.; Russell, G.; Fagerhol, M. K. Calprotectin as a marker of inflammation in cystic fibrosis. Arch Dis Child 74:136-139; 1996.
54. Tibble, J. A.; Bjarnason, I. Fecal calprotectin as an index of intestinal inflammation. Drugs Today (Barc) 37:85-96; 2001.
55. Nakamura, T.; Kido, J.; Kido, R.; Ohishi, K.; Yamauchi, N.; Kataoka, M.; Nagata, T. The association of calprotectin level in gingival crevicular fluid with gingival index and the activities of collagenase and aspartate aminotransferase in adult periodontitis patients. J Periodontol 71:361-367; 2000.
56. Dunlop, 0.; Bruun, J. N.; Myrvang, B.; Fagerhol, M. K. Calprotectin in cerebrospinal fluid of the HIV infected: a diagnostic marker of opportunistic central nervous system infection? Scand J Infect Dis 23:687-689; 1991.
57. Muller, F.; Froland, S. S.; Aukrust, P.; Fagerhol, M. K. Elevated serum calprotectin levels in HIV-infected patients: the calprotectin response during ZDV treatment is associated with clinical events. J Acquir Immune Defic Syndr 7:931-939; 1994.
58. Brun, J. G.; Haga, H. J.; Boe, E.; Kallay, I.; Lekven, C.; Berntzen, H. B.; Fagerhol, M. K. Calprotectin in patients with rheumatoid arthritis: relation to clinical and laboratory variables of disease activity. J Rheumatol 19:859-862; 1992.
59. Daley, J. M.; Reichner, J. S.; Mahoney, E. J.; Manfield, L.; Henry, W. L., Jr.; Mastrofrancesco, B.; Albina, J. E. Modulation of macrophage phenotype by soluble product(s) released from neutrophils. J Immunol 174:2265-2272; 2005.
60. Halle, J. N.; Kasper, C. E.; Gidday, J. M.; Koos, B. J. Enhancing adenosine A1 receptor binding reduces hypoxic-ischemic brain injury in newborn rats. Brain Res 759:309-312; 1997.

61. Chen, G. J.; Harvey, B. K.; Shen, H.; Chou, J.; Victor, A.; Wang, Y. Activation of adenosine A3 receptors reduces ischemic brain injury in rodents. J Neurosci Res 84:1848-1855; 2006.
62. Reece, T. B.; Okonkwo, D. O.; Ellman, P. I.; Maxey, T. S.; Tache-Leon, C.; Warren, P. S.; Laurent, J. J.; Linden, J.; Kron, I. L.; Tribble, C. G.; Kern, J. A. Comparison of systemic and retrograde delivery of adenosine A2A agonist for attenuation of spinal cord injury after thoracic aortic cross-clamping. Ann Thorac Surg 81:902-909; 2006. Dovi J V, He L K, DiPietro L A. Accelerated wound closure in neutrophil-depleted mice. J Leukoc Biol. 2003; 73: 448-55.
63. Dovi J V, He L K, DiPietro L A. Accelerated wound closure in neutrophil-depleted mice. J Leukoc Biol. 2003; 73: 448-55.
64. Gajendrareddy P K, Sen C K, Horan M P, Marucha P T. Hyperbaric oxygen therapy ameliorates stress-impaired dermal wound healing. Brain Behav Immun 2005; 19: 217-22.
65. Glaser R, Kiecolt-Glaser J K, Marucha P T, MacCallum R C, Laskowski B F, Malarkey W B. Stress-related changes in proinflammatory cytokine production in wounds. Arch Gen Psychiatry. 1999; 56: 450-6.
66. Godbout J P, Glaser R. Stress-induced immune dysregulation: implications for wound healing, infectious disease and cancer. J Neuroimmune Pharmacol. 2006; 1: 421-7. Epub 2006 Aug. 10.
67. Kiecolt-Glaser J K, Marucha P T, Malarkey W B, Mercado A M, Glaser R. Slowing of wound healing by psychological stress. Lancet 1995; 346: 1194-6.
68. Marucha P T, Kiecolt-Glaser J K, Favagehi M. Mucosal wound healing is impaired by examination stress. Psychosom Med 1998; 60: 362-5.
69. Mercado A M, Quan N, Padgett D A, Sheridan J F, Marucha P T. Restraint stress alters the expression of interleukin-1 and keratinocyte growth factor at the wound site: an in situ hybridization study. J Neuroimmunol 2002; 129: 74-83.
70. Padgett D A, Marucha P T, Sheridan J F. Restraint stress slows cutaneous wound healing in mice. Brain Behav Immun 1998; 12: 64-73.
71. Rojas I G, Padgett D A, Sheridan J F, Marucha P T. Stress-induced susceptibility to bacterial infection during cutaneous wound healing. Brain Behav Immun 2002; 16: 74-84.
72. Savill J S, Wyllie A H, Henson J E, Walport M J, Henson P M, Haslett C. Macrophage phagocytosis of aging neutrophils in inflammation. Programmed cell death in the neutrophil leads to its recognition by macrophages. J Clin Invest. 1989; 83: 865-75.
73. Thomas D W, O'Neill I D, Harding K G, Shepherd J P. Cutaneous wound healing: a current perspective. J Oral Maxillofac Surg 1995; 53: 442-7.
74. Tugizov S, Berline J, Herrera R, Penaranda M E, Nakagawa M, Palefsky J. Inhibition of human papillomavirus type 16 E7 phosphorylation by the S100 MRP-8/14 protein complex. J Virol 2005; 79: 1099-112.
75. Yui S, Nakatani Y, Mikami M. Calprotectin (S100A8/S100A9), an inflammatory protein complex from neutrophils with a broad apoptosis-inducing activity. Biol Pharm Bull 2003; 26: 753-60.

I claim:

1. A method for reducing deleterious effects of tissue hypoxia, an infarct, ischemia, atherosclerosis, reperfusion, toxic shock, septic shock and/or psychological or physical stress in a patient in need thereof, said method comprising the step of:
administering to the patient a composition comprising a S100A8 protein or a mutant protein containing a serine residue in place of a cysteine residue at position 42 of S100A8, and a pharmaceutically acceptable carrier, in an amount sufficient to reduce deleterious effects of tissue hypoxia, an infarct, ischemia, atherosclerosis, reperfusion and/or psychological or physical stress in a patient,
whereby said patient benefits from administration of the protein.

2. The method of claim 1 wherein said step of administering is intravenous injection.

3. The method of claim 1, wherein said step of administering is intrasynovial administration.

4. The method of claim 1, wherein said step of administering is within 0.5 minutes to 24 hours of an ischemia or an infarct.

5. The method of claim 4, wherein said step of administering is within 0.5 min to 6 hours of the ischemia or infarct.

6. The method of claim 5, wherein the step of administering is within 0.5 min to 1 hour of the ischemia or infarct.

7. The method of claim 1, wherein the infarct is a cardiac infarct or a cerebral infarct.

8. The method of claim 1, wherein patient is suffering from psychological stress.

9. The method of claim 8, wherein the step of administering is on a daily basis.

10. The method of claim 1, wherein the tissue hypoxia is due to physical exertion.

11. The method of claim 10, wherein the step of administering is from 0.5 min to 24 hours prior to the physical exertion and up to about 24 hours after the physical exertion.

12. The method of claim 1, wherein the step of administering is from 4 hours prior to reperfusion and up to 24 hours after reperfusion.

13. The method of claim 12, wherein the step of administering is simultaneous with reperfusion up to 4 hours after reperfusion.

14. The method of claim 1, wherein the composition is administered at a dose from about 0.05 to about 100 mg/kg body weight.

15. The method of claim 1 wherein the composition is administered at a dose from about 0.25 to about 10 mg/kg body weight.

* * * * *